US010479820B2

(12) United States Patent
Blattner et al.

(10) Patent No.: US 10,479,820 B2
(45) Date of Patent: Nov. 19, 2019

(54) **ENHANCED PRODUCTION OF RECOMBINANT CRM197 IN *E. COLI***

(71) Applicant: SCARAB GENOMICS, LLC, Madison, WI (US)

(72) Inventors: Cristopher R. Blattner, Madison, WI (US); David Frisch, Fitchburg, WI (US); Robert E. Novy, Verona, WI (US); Terrance M. Henker, Madison, WI (US); Eric A. Steffen, Mount Horeb, WI (US); Frederick R. Blattner, Madison, WI (US); Hyunsic Choi, Madison, WI (US); Gyorgy Posfai, Szeged (HU); Charles F. Landry, Fitchburg, WI (US)

(73) Assignee: SCARAB GENOMICS, LLC, Madison, WI (US)

( * ) Notice: Subject to any disclaimer, the term of this patent is extended or adjusted under 35 U.S.C. 154(b) by 345 days.

(21) Appl. No.: 15/122,891

(22) PCT Filed: Mar. 2, 2015

(86) PCT No.: PCT/US2015/018338
§ 371 (c)(1),
(2) Date: Aug. 31, 2016

(87) PCT Pub. No.: WO2015/134402
PCT Pub. Date: Sep. 11, 2015

(65) Prior Publication Data
US 2017/0073379 A1  Mar. 16, 2017

Related U.S. Application Data

(60) Provisional application No. 61/947,234, filed on Mar. 3, 2014.

(51) Int. Cl.
*C07K 14/34* (2006.01)
*C12N 1/08* (2006.01)
*C12N 1/20* (2006.01)
*C12N 15/70* (2006.01)

(52) U.S. Cl.
CPC .............. *C07K 14/34* (2013.01); *C12N 1/08* (2013.01); *C12N 1/20* (2013.01)

(58) Field of Classification Search
None
See application file for complete search history.

(56) References Cited

U.S. PATENT DOCUMENTS

| 2005/0260720 A1 | 11/2005 | Ito et al. | |
| 2009/0104667 A1 | 4/2009 | Asakura et al. | |
| 2011/0028423 A1* | 2/2011 | Otsuki | A01N 35/10 514/49 |
| 2012/0128727 A1 | 5/2012 | Baglioni et al. | |
| 2012/0214213 A1* | 8/2012 | Chen | C12N 9/88 435/135 |
| 2012/0289688 A1 | 11/2012 | Blais et al. | |
| 2013/0011874 A1 | 1/2013 | Campbell et al. | |
| 2016/0251609 A1* | 9/2016 | Blattner | C12N 1/08 435/69.1 |

FOREIGN PATENT DOCUMENTS

WO    WO-2009105551 A1 *   8/2009   ............... C12N 9/93

OTHER PUBLICATIONS

Gustaffson et al. Trends in Biotechnology 22, 7 346-353 (Year: 2004).*
Horler, R.S., et al., "Furanose-specific sugar transport: characterization of a bacterial galactofuranose-binding protein," J . Biol. Chem., vol. 284, No. 45, pp. 31156-31163 (Sep. 10, 2009).
Posfai, G., et al., "Reduced Genome *Escherichia coli*: A pllatform for genomic and metabolic engineering." Metabolomics and Environmental Biotechnology EC-US Tak Force on Biotechnology Research, pp. 44, Abstract P17, Abstract (Jun. 16-17, 2008).
International Search Report of PCT/U2015/18338 dated Jun. 19, 2015.
Written Opinion of PCT/U2015/18338 dated Jun. 19, 2015.
Hayashi, K., et al., "Highly Accurate Genome Sequences of *Escherichia coli* K-12 Strains MG1655 and W3110," Molecular Systems Biology, vol. 2, Issue 1, pp. 1-5 (Feb. 21, 2006).
Durfee, T., et al., "The Complete Genome Sequence of *Escherichia coli* DH10B: Insights into the Biology of a Laboratory Workhorse," Journal of Bacteriology, vol. 190, No. 7, pp. 2597-2606 (Apr. 2008).

* cited by examiner

*Primary Examiner* — Nancy A Treptow
(74) *Attorney, Agent, or Firm* — Polsinelli PC; Christopher M. Cabral

(57) ABSTRACT

Rediced genome or native K12 strain *E. coli* bacteria comprising expression vectors encoding a recombinant CRM197 protein and their use in the production of CRM 197 is provided. The CRM 197 protein may be fused to a signal sequence that directs the expressed CRM197 protein to the periplasm of the *E. coli* host.

33 Claims, 25 Drawing Sheets

Specification includes a Sequence Listing.

Figure 8
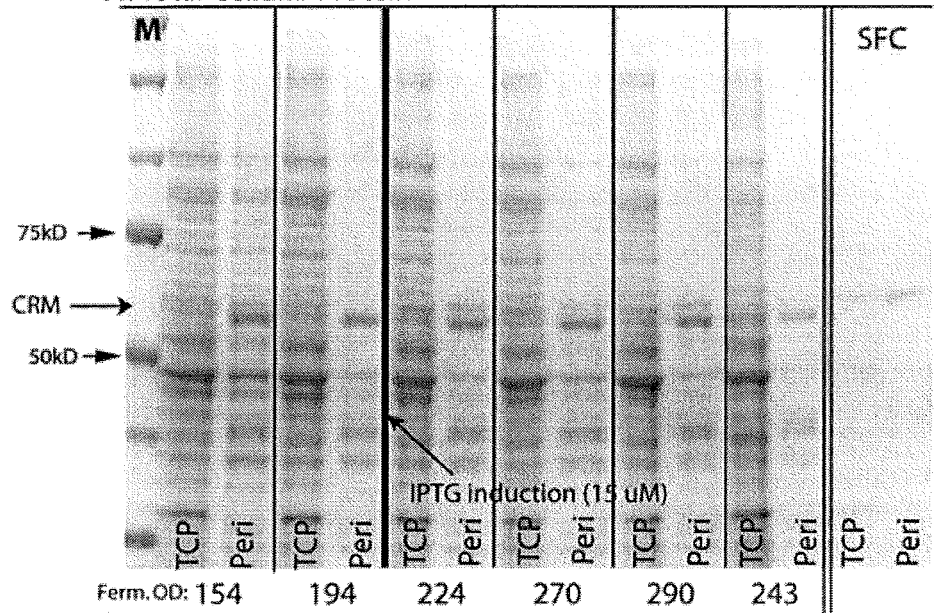
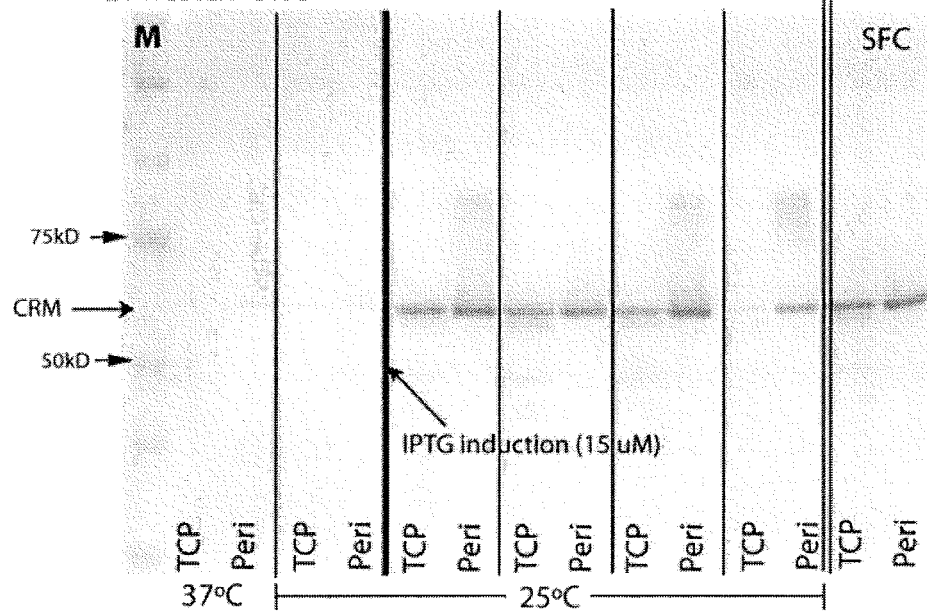

Figure 10
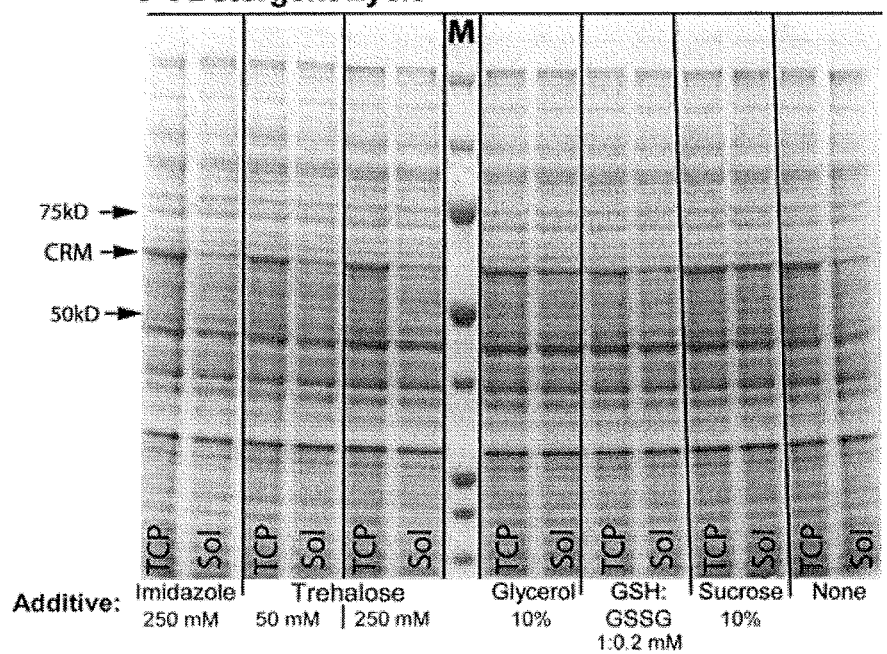
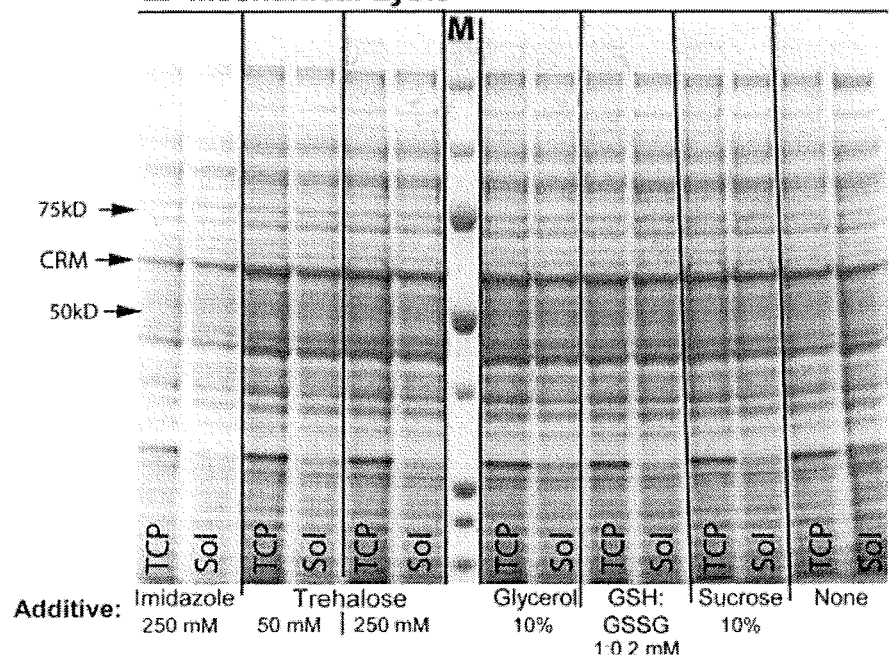

Figure 16

A. Expressed CRM197 synthetic nucleic acid sequence (SEQ ID NO: 1)

GGTGCGGATGATGTTGTGGACAGCTCTAAGTCTTTTGTGATGGAAAACTTT
AGCTCGTACCACGGTACGAAGCCAGGTTATGTCGACAGCATTCAAAAGG
TATCCAGAAACCGAAGTCCGGCACGCAGGGTAACTACGACGACGATTGGA
AAGAGTTCTACAGCACCGACAACAAGTATGACGCAGCGGGTTACAGCGTT
GACAATGAGAATCCGTTGAGCGGCAAAGCGGGTGGTGTTGTCAAAGTGAC
GTATCCGGGTCTGACCAAGGTCCTGGCGTTGAAAGTTGATAACGCGGAAA
CCATTAAGAAAGAGCTGGGTCTGAGCCTGACCGAGCCGTTGATGGAGCAA
GTTGGTACCGAAGAGTTTATCAAACGTTTCGGCGATGGTGCGAGCCGCGT
TGTCCTGTCCCTGCCTTTCGCGGAGGGCAGCTCCAGCGTTGAGTATATCAA
TAACTGGGAGCAAGCAAAAGCGCTGTCCGTCGAACTGGAAATCAATTTTG
AAACGCGCGGTAAACGTGGTCAAGATGCAATGTACGAGTATATGGCCCAG
GCCTGCGCTGGTAATCGTGTTCGTCGCAGCGTTGGTAGCAGCTTGTCTTGT
ATCAACCTGGATTGGGATGTGATCCGTGATAAGACCAAGACTAAGATCGA
GAGCCTGAAAGAACATGGCCCGATTAAGAACAAGATGTCGGAGAGCCCG
AATAAGACCGTGAGCGAAGAAAAGGCCAAGCAGTATCTGGAAGAGTTCC
ACCAAACGGCTCTGGAGCATCCGGAGCTGAGCGAGCTGAAAACGGTTACG
GGCACCAACCCGGTGTTCGCAGGTGCGAATTACGCGGCGTGGGCAGTGAA
TGTGGCGCAGGTCATCGACTCCGAAACGGCGGACAATTTGGAGAAAACCA
CCGCAGCGCTGAGCATTCTGCCGGGCATCGGCAGCGTTATGGGCATTGCA
GATGGTGCTGTGCACCATAACACTGAAGAAATCGTAGCGCAAAGCATTGC
CCTGTCTAGCTTGATGGTGGCGCAGGCTATTCCGCTGGTCGGCGAACTGGT
TGATATCGGCTTTGCTGCCTACAACTTCGTTGAAAGCATCATTAACCTGTT
TCAGGTGGTCCACAACAGCTATAATCGCCCAGCGTACAGCCCGGGTCACA
AGACCCAACCGTTCCTGCACGATGGCTATGCGGTGTCTTGGAACACGGTC
GAAGATAGCATCATTCGTACCGGTTTCCAGGGCGAGAGCGGCCATGACAT
CAAGATTACTGCAGAAAATACCCCGCTGCCGATCGCAGGTGTCCTGCTGC
CTACGATTCCGGGTAAGCTGGACGTTAACAAAAGCAAAACCCACATTTCT
GTGAACGGTCGTAAGATTCGCATGCGTTGTCGTGCGATTGACGGCGACGT
CACCTTCTGCCGTCCGAAGAGCCCGGTCTACGTTGGTAATGGTGTGCACGC
GAACCTGCACGTGGCGTTTCACCGCAGCAGCTCGGAGAAATCCATAGCA
ATGAGATTTCTAGCGACAGCATTGGCGTTCTGGGTTACCAAAAGACGGTT
GACCATACCAAAGTCAATTCCAAACTGAGCCTGTTCTTTGAGATCAAAAG
CTAA

Figure 16 - Continued

B. Expressed CRM197 synthetic nucleic acid sequence (SEQ ID NO:3)
atgGGCGCAGATGACGTAGTAGACAGCAGCAAAAGCTTCGTGATGGAA
AACTTTAGCTCGTACCACGGTACGAAGCCAGGTTATGTCGACAGCATT
CAAAAAGGTATCCAGAAACCGAAGTCCGGCACGCAGGGTAACTACGA
CGACGATTGGAAAGAGTTCTACAGCACCGACAACAAGTATGACGCAG
CGGGTTACAGCGTTGACAATGAGAATCCGTTGAGCGGCAAAGCGGGT
GGTGTTGTCAAAGTGACGTATCCGGGTCTGACCAAGGTCCTGGCGTT
GAAAGTTGATAACGCGGAAACCATTAAGAAAGAGCTGGGTCTGAGCC
TGACCGAGCCGTTGATGGAGCAAGTTGGTACCGAAGAGTTTATCAAA
CGTTTCGGCGATGGTGCGAGCCGCGTTGTCCTGTCCCTGCCTTTCGC
GGAGGGCAGCTCCAGCGTTGAGTATATCAATAACTGGGAGCAAGCAA
AAGCGCTGTCCGTCAACTGGAAATCAATTTTGAAACGCGCGGTAAA
CGTGGTCAAGATGCAATGTACGAGTATATGGCCCAGGCCTGCGCTGG
TAATCGTGTTCGTCGCAGCGTTGGTAGCAGCTTGTCTTGTATCAACCT
GGATTGGGATGTGATCCGTGATAAGACCAAGACTAAGATCGAGAGCC
TGAAAGAACATGGCCCGATTAAGAACAAGATGTCGGAGAGCCCGAAT
AAGACCGTGAGCGAAGAAAGGCCAAGCAGTATCTGGAAGAGTTCCA
CCAAACGGCTCTGGAGCATCCGGAGCTGAGCGAGCTGAAAACGGTTA
CGGGCACCAACCCGGTGTTCGCAGGTGCGAATTACGCGGCGTGGGCA
GTGAATGTGGCGCAGGTCATCGACTCCGAAACGGCGGACAATTTGGA
GAAAACCACCGCAGCGCTGAGCATTCTGCCGGGCATCGGCAGCGTTA
TGGGCATTGCAGATGGTGCTGTGCACCATAACACTGAAGAAATCGTA
GCGCAAAGCATTGCCCTGTCTAGCTTGATGGTGGCGCAGGCTATTCC
GCTGGTCGGCGAACTGGTTGATATCGGCTTTGCTGCCTACAACTTCGT
TGAAAGCATCATTAACCTGTTTCAGGTGGTCCACAACAGCTATAATCG
CCCAGCGTACAGCCCGGGTCACAAGACCCAACCGTTCCTGCACGATG
GCTATGCGGTGTCTTGGAACACGGTCGAAGATAGCATCATTCGTACC
GGTTTCCAGGGCGAGAGCGGCCATGACATCAAGATTACTGCAGAAAA
TACCCCGCTGCCGATCGCAGGTGTCCTGCTGCCTACGATTCCGGGTA
AGCTGGACGTTAACAAAAGCAAAACCCACATTTCTGTGAACGGTCGTA
AGATTCGCATGCGTTGTCGTGCGATTGACGGCGACGTCACCTTCTGC
CGTCCGAAGAGCCCGGTCTACGTTGGTAATGGTGTGCACGCGAACCT
GCACGTGGCGTTTCACCGCAGCAGCTCGGAGAAATCCATAGCAATG
AGATTTCTAGCGACAGCATTGGCGTTCTGGGTTACCAAAAGACGGTT
GACCATACCAAAGTCAATTCCAAACTGAGCCTGTTCTTTGAGATCAAA
AGCtaa

Figure 16 – Concluded

C. Expressed, Processed CRM197 Synthetic amino acid sequence (SEQ ID NO: 2)

GADDVVDSSKSFVMENFSSYHGTKPGYVDSIQKGIQKPKSGTQGNYDDDWK
EFYSTDNKYDAAGYSVDNENPLSGKAGGVVKVTYPGLTKVLALKVDNAETI
KKELGLSLTEPLMEQVGTEEFIKRFGDGASRVVLSLPFAEGSSSVEYINNWEQ
AKALSVELEINFETRGKRGQDAMYEYMAQACAGNRVRRSVGSSLSCINLDW
DVIRDKTKTKIESLKEHGPIKNKMSESPNKTVSEEKAKQYLEEFHQTALEHPEL
SELKTVTGTNPVFAGANYAAWAVNVAQVIDSETADNLEKTTAALSILPGIGSV
MGIADGAVHHNTEEIVAQSIALSSLMVAQAIPLVGELVDIGFAAYNFVESIINLF
QVVHNSYNRPAYSPGHKTQPFLHDGYAVSWNTVEDSIIRTGFQGESGHDIKIT
AENTPLPIAGVLLPTIPGKLDVNKSKTHISVNGRKIRMRCRAIDGDVTFCRPKS
PVYVGNGVHANLHVAFHRSSSEKIHSNEISSDSIGVLGYQKTVDHTKVNSKLS
LFFEIKS

Signal Peptides of Major Periplasmic Proteins

| Most abundant K-Strain | Additional candidates B-Strain |
|---|---|
| malE | fkpA |
| hdeA | glnH |
| oppA | ytfQ |
| hdeB | |
| mglB | |
| agp | |
| rbsB | |

*Extrapolated to $OD_{600}$ = 250

ENHANCED PRODUCTION OF RECOMBINANT CRM197 IN *E. COLI*

CROSS-REFERENCE TO RELATED APPLICATIONS

This application is the 35 U.S.C. 371 National Stage of International Application Number PCT/US2015/018338, filed Mar. 2, 2015, which claims the benefit of U.S. Provisional Application No. 61/947,234 filed Mar. 3, 2014, the contents of each of which are incorporated herein by reference.

SEQUENCE LISTING SUBMISSION VIA EFS-WEB

A computer readable text file, entitled "010447-5037-US-Sequence-Listing_ST25.txt," created on or about Aug. 30, 2016, with a file size of about 22 KB contains the sequence listing for this application and is hereby incorporated by reference in its entirety.

FIELD OF THE INVENTION

The present invention is directed to the production of recombinant CRM197 in *E. coli*, preferably in reduced genome *E. coli* K12 strains.

BACKGROUND OF THE INVENTION

Diphtheria toxin (DTx) is a two-component exotoxin of *Corynebacterium diphtheriae* synthesized as a single polypeptide chain of 535 amino acids containing an A (active) domain and a B (binding) domain linked together by a disulfide bridge. The toxin binds to a cell receptor (HB-EGF receptor) and enters the cell by endocytosis where the A domain is released from the B domain by proteolytic cleavage. The A domain then exits the endosome through pores made by the B domain and enters the cytoplasm where it inhibits protein synthesis ultimately resulting in cell death.

CRM197 is a mutated form of Dtx containing a single amino acid substitution of glutamic acid for glycine (G52E) that renders the protein enzymatically inactive and nontoxic. CRM197 has been found to be an ideal carrier for conjugate vaccines against encapsulated bacteria. Conjugate vaccines comprise CRM197 covalently linked to poorly immunogenic and T-cell independent capsular polysaccharides, thus creating conjugate antigens that are highly immunogenic and result in long-lasting immunity against the antigen(s).

Vaccines containing CRM197 as a carrier protein have been successfully used to immunize millions of children and include Menveo®, a tetravalent conjugate vaccine against serogroups A-C-W135-Y of *Neisseria meningitidis*, Menjugate® and Meningitec® (against serotype C of *N. meningitidis*), Vaxem-Hib® and HibTITER® (against *Haemophilus influenzae* type B, Hib), and the multivalent pneumococcal conjugate Prevnar™.

In contrast to tetanus and diphtheria toxins, CRM197 does not require chemical detoxification and can therefore be purified to homogeneity and used directly for conjugation. CRM197 is currently manufactured by the fermentation of either *Corynebacterium diphtheriae* C7, where it is expressed from multiple lysogens of the β phage, or from a plasmid system in *Pseudomonas flurorescens*. The yield of CRM197 (which is released into the media during *C. diphtheriae* fermentation) is low ranging from tens of mg/L to ~200 mg/L and requires biosafety level 2 facilities, resulting in a retail price of about $500 US per milligram of CRM197. A single dose of vaccine typically contains about 10 and 60 µg of CRM197 and over 150 million doses are used each year. Current demand for conjugate CRM197 vaccines has outpaced supply and has resulted in delays in initiating vaccination programs in developing countries placing the health of millions of children at risk.

Moreover, a possible therapeutic use for CRM197 in treating cancers such as ovarian cancer has recently been reported, based on CRM197's ability to bind the soluble form of heparin-binding epidermal growth factor (pro-HB-EGF), which is highly expressed in some cancers. The research and development of this therapeutic potential places even more of a strain on current production methods.

The single greatest factor contributing to the high price and short supply of CRM197 is the historical inability to generate high amounts of CRM197 in the production workhorse *E. coli*. Although an insoluble form of CRM197 can be fermented in *E. coli* to relatively moderate yields, only a fraction of the insoluble product can be converted to the soluble form (Stefan et al., 2011). Producing high amounts of soluble CRM197 in *E. coli* has been even more challenging. A method for reliably and inexpensively producing high amounts of CRM197 for therapeutic use would constitute a significant advance in the art.

SUMMARY OF THE INVENTION

The present invention relates to a method for producing a recombinant CRM197 protein in an *E. coli* host cell. In several embodiments, the method comprises incubating a reduced genome *E. coli* comprising an expression vector comprising a nucleic acid sequence encoding a CRM197 protein operably linked to an expression control sequence under conditions suitable for the expression of the recombinant CRM197 protein. A significant increase in yield of CRM197 is achieved in a reduced genome *E. coli* host cell according to the invention compared to production in wild type *E. coli* strains such as BL21. The nucleic acid sequence encoding the CRM197 protein is preferably codon-optimized for expression in an *E. coli* host cell. In a preferred embodiment, the native parent *E. coli* strain is a K12 strain. In another embodiment, the method comprises incubating a native K12 strain *E. coli* comprising an expression vector comprising a nucleic acid sequence encoding a CRM197 protein operably linked to an expression control sequence under conditions suitable for the expression of the recombinant CRM197 protein In one aspect, the nucleic acid sequence encoding a CRM197 protein is fused to a nucleic acid sequence encoding a signal sequence that directs transfer of the CRM197 protein to the periplasm of the *E. coli* host cell (preferably a reduced genome *E. coli* host cell), whereby a yield of about 1 gram per liter to about 10 grams per liter of soluble CRM197 is achieved. According to this aspect of the invention, the *E. coli* host (preferably a reduced genome *E. coli* host) comprises an expression vector comprising a nucleic acid sequence comprising a 5' signal sequence portion encoding a polypeptide having an amino acid sequence capable of directing transport of CRM197 to the *E. coli* periplasm and a 3' CRM197 portion encoding the CRM197 protein lacking its native signal sequence. Preferably the expression of CRM197 is inducible and the method comprises the steps of (a) growing the *E. coli* (preferably a reduced genome *E. coli*) and (b) inducing expression of CRM197. Preferably, the method is carried out in a fermentor.

In related aspects, the (e.g. reduced genome) *E. coli* host cell is transformed with an expression vector comprising an inducible promoter (e.g. a lac derivative promoter) operatively linked to the protein coding sequence and expression of CRM197 is induced by the addition of a suitable amount of inducer (e.g. Isopropyl β-D-1-thiogalactopyranoside (IPTG)). Preferably, under shake flask conditions, induction occurs at an optical density (OD) at 600 nm (at which wavelength 1 OD unit corresponds to about $0.8 \times 10^9$ cells/ml) of about 0.1 to about 1.5 (more preferably about 0.2 to about 0.9, even more preferably about 0.3 to about 0.6). Under fermentation conditions, induction preferably occurs at an OD600 of about 100 to 400, more preferably about 150 to 300, most preferably between 200 to 275 (e.g. 230 and 250). In other related aspects, the pH of the culture during growth and/or induction is from about 6.5 to about 7.5, the growth and/or induction temperature is from about 20° C. to about 30° C. (preferably about 25° C.) and the growth media is free of serum, yeast extract and animal-derived by-products. In particularly preferred embodiments, growing the (e.g. reduced genome) *E. coli* comprises a relatively short initial incubation at 37° C. (e.g. 1 to 3 hours) followed by growth at 20° C. to 30° C. (preferably at about 25° C.) prior to and subsequent to induction or comprises continuous growth at 20° C. to 30° C. (preferably at about 25° C.) prior to and subsequent to induction.

In related embodiments, the yield of soluble CRM197 obtained is at least about 0.5 g/L, at least about 0.7 g/L, at least about 1.0 g/L, at least about 1.3 g/L, at least about 1.5 g/L, at least about 1.7 g/L, at least about 2.0 g/L, at least about 2.3 g/L, at least about 2.5 g/L, at least about 2.7 g/L, at least about 3.0 g/L, at least about 3.5 g/L, at least about 3.7 g/L, at least about 4.0 g/L, at least about 4.5 g/L, at least about 5 g/L, at least about 5.5 g/L, at least about 6.0 g/L, at least about 7.0 g/L, at least about 8.0 g/L, at least about 9.0 g/L or at least about 10.0 g/L. In other embodiments, the yield of soluble CRM197 obtained is from about 1.0 g/L to about 10.0 g/L, from about 1.0 g/L to about 9.0 g/L, from about 1.0 g/L to about 8.0 g/L, from about 1.0 g/L to about 7.0 g/L, from about 1.0 g/L to about 6.0 g/L, from about 1.0 g/L to about 5.0 g/L, from about 1.0 g/L to about 4.0 g/L, from about 1.0 g/L to about 3.0 g/L or from about 1.0 g/L to about 2.0 g/L. In other embodiments, the yield of soluble CRM197 obtained is from about 2.0 g/L to about 10.0 g/L, from about 2.0 g/L to about 9.0 g/L, from about 2.0 g/L to about 8.0 g/L, from about 2.0 g/L to about 7.0 g/L, from about 2.0 g/L to about 6.0 g/L, from about 2.0 g/L to about 5.0 g/L, from about 2.0 g/L to about 4.0 g/L, from about 2.0 g/L to about 4.0 g/L or from about 2.0 g/L to about 3.0 g/L. In other embodiments, the yield of soluble CRM197 obtained is from about 3.0 g/L to about 10.0 g/L, from about 3.0 g/L to about 9.0 g/L, from about 3.0 g/L to about 8.0 g/L, from about 3.0 g/L to about 7.0 g/L, from about 3.0 g/L to about 6.0 g/L, from about 3.0 g/L to about 5.0 g/L, or from about 3.0 g/L to about 4.0 g/L.

In a related aspect, the 5' signal sequence portion encodes a signal recognition particle (SRP) dependent signal sequence such as the DsbA, TolB and TorT secretion signals, a Sec-dependent signal sequence such as the OmpF, OmpT, OmpA, PhoA, MalE, LamB, LivK and PelB secretion signals, or a twin arginine translocation (TAT) signal sequence such as the TorA and Sufi secretion signals. In some embodiments, the 5' signal sequence portion encodes a Sec-dependent signal sequence, preferably the OmpA or OmpF secretion signal. In a particularly preferred embodiment, the 5' signal sequence portion encodes the ompF secretion signal.

In other preferred embodiments, the 5' signal sequence portion encodes a signal sequence selected from an MglB, MalE, OppA, RbsB, Agp, FkpA, YtfQ, HdeA, HdeB, OmpC and GlnH secretion signal. In a particularly preferred embodiment, the 5' signal sequence portion encodes the YtfQ secretion signal.

In another related aspect, the *E. coli* host cell additionally comprises one or more nucleic acids comprising a sequence encoding one or more proteins for assisting the translocation and/or folding of CRM197 in the periplasm, operably linked to an expression control sequence. The nucleic acid(s) comprising a sequence encoding one or more proteins for assisting the translocation and/or folding of CRM197 in the periplasm may be part of the same expression vector comprising the nucleotide sequence encoding CRM197 or may be located on a different expression vector. Proteins for assisting the translocation and/or folding of CRM197 include, without limitation, chaperones such as Skp, DnaK, DnaJ, CaflM, and CaflA; disulfide bond formation proteins such as DsbA, DsbB, DsbC and DsbD; peptidyl-prolyl cis-trans isomerases such as PpiA, PpiD, FkpA and SurA; soluble partner proteins such as MBP, GST, and thioredoxin; secretion pathway proteins such as YebF, MalE, HlyA, Hirudin, OmpF, and Spy; protease inhibitors such as YccA; and proteins that relieve export saturation such as PspA.

In another embodiment, the nucleotide sequence encoding a CRM197 protein is not fused to a signal sequence, whereby a yield of insoluble CRM197 of about 2 grams per liter to about 25 grams per liter is achieved. According to this aspect of the invention, the (e.g. reduced genome) *E. coli* host comprises an expression vector comprising a nucleic acid sequence encoding a CRM197 protein lacking its native signal sequence, whereby the CRM197 protein is expressed in the cytoplasm of the *E. coli* host.

In several aspects, the present invention relates to a method for producing a recombinant CRM197 protein in a (e.g. reduced genome) *E. coli* host cell, the method comprising: ligating into an expression vector a nucleotide sequence encoding a CRM197 protein fused to a signal sequence that directs transfer of the CRM197 protein to the periplasm; transforming the *E. coli* host cell with the expression vector; and culturing the transformed *E. coli* host cell in a culture media suitable for the expression of the recombinant CRM197 protein; wherein the yield of soluble CRM197 is about 1 to 10 g/L, preferably about 2 to 10 g/L, and further comprising harvesting the *E. coli* cells from the culture and lysing the harvested cells by a mechanical method in the absence of detergent. Optionally, the method further comprises obtaining a soluble fraction of the resulting lysate (e.g. by centrifugation to separate a soluble and insoluble fraction) and subjecting the soluble fraction (comprising soluble CRM197 produced by the *E. coli* host) to one or more purification steps. In one embodiment the soluble CRM197 is subjected to hydrophobic interaction chromatography and/or anion exchange chromatography. In preferred embodiments, the *E. coli* host cell is a reduced genome *E. coli* host cell.

In other aspects, the invention relates to a (e.g. reduced genome) *E. coli* host cell comprising an expression vector, the expression vector comprising a nucleic acid sequence comprising nucleic acid sequence comprising a 5' signal sequence portion encoding a polypeptide having an amino acid sequence capable of directing transport of CRM197 to the *E. coli* periplasm and a 3' CRM197 portion encoding the CRM197 protein lacking its native signal sequence operably linked to an expression control sequence. In preferred embodiments, the *E. coli* host cell is a reduced genome *E. coli* host cell that lacks at least the genes deleted from reduced genome *E. coli* strain MDS42 or lacks at least the genes deleted from reduced genome *E. coli* strain MDS69.

These and other embodiments of the present invention are described in more detail herein below.

DESCRIPTION OF THE DRAWINGS

FIG. 10 depicts protein gels of detergent and mechanical lysis and CRM197 solubility. MDS42recA cells carrying an expression vector encoding ompA fused to CRM197 were subjected to fed-batch fermentation as described for FIG. 8. Cells were lysed using either (A) detergent (Bugbuster® (Novagen), a proprietary mixture of non-ionic detergents that disrupt the cell membrane) or (B) mechanical (sonication) lysis in the presence of solubilization agents. Note that lysis in the absence of detergent resulted in high levels of soluble CRM197. GSH:GSSG=reduced to oxidized ratio of glutathione; M=marker; Sol=soluble fraction; TCP=total cell protein. Inducer (IPTG)=35 μM.

FIG. 11 is a graph depicting fermentation of MDS69 metab host cells carrying an expression vector encoding OmpA-CRM197. CRM197 was found to increase in fed-batch fermentation up to the 30 hour time point where a maximum yield of 1.95 g/L was achieved.

FIG. 12 depicts protein gels from the fermentation of FIG. 11 showing a high amount of soluble CRM197 in fermentation samples. Strain MDS69 metab was subjected to fed-batch fermentation in minimal media with glucose as the carbon source. Samples collected prior to the addition of inducer (22 hrs) or at either 28 or 29 hrs were homogenized by sonication and different cellular fractions isolated. CRM197 was found exclusively in the soluble (Sol) fraction. TCP=total cellular protein fraction; Insol=insoluble fraction.

FIG. 13 depicts the results of a two column purification of CRM197. Panel A: 50 OD of the 28 hr fermentation sample shown in FIG. 12 was subjected to microfluidizer (MF) homogenization. Soluble and insoluble (IS) fractions were isolated and soluble material (25 OD equivalents) was loaded onto a phenyl sepharose column. The three lanes labeled "Soluble" are 0.1, 0.07 and 0.04 OD of pre-loaded soluble samples, respectively. CRM197-containing material was eluted with 10 mM NaCl, 10 mM phosphate buffer, pH 7.5. Five consecutive 2.5 ml samples were collected (left to right) and fractions indicated by a circle were pooled. Note the small amount of unprocessed CRM197 (arrows) that was purified away from the main eluted sample and found following elution using distilled water only. Panel B: Pooled samples from Panel A were loaded onto a DEAE sepharose column and eluted using different salt concentrations (0.1 M NaCl followed by 1 M NaCl and finally, 1.5 M NaCl). CRM197 of highest purity was eluted at 1 M NaCl. Anti-diphtheria toxin antibody (1:1000 dilution) Western blots are shown alongside protein-stained gels run in parallel. F, flow through; W, column wash; MF=total homogenate following microfluidization; IS=insoluble fraction following centrifugation of microfluidization homogenate; S=soluble fraction following centrifugation of microfluidization homogenate.

FIG. 14 protein gel analysis of CRM197 expression in MDS42recA compared to wild type B strain BLR(DE3). Cells were transformed with an expression vector encoding an ompA-CRM197 fusion directing the protein to the periplasm and grown at 25° C. for 19 hours in shaken flasks. Expression of CRM197 was induced at OD=0.3 (late stage) by addition of IPTG at the indicated concentrations. Periplasmic proteins were isolated and analyzed. Note the endogenous *E. coli* protein that migrates directly below CRM197.

FIG. 15 protein gel analysis of the periplasmic fractions generated from pSX2-OmpA CRM197 and pSX2-OmpF CRM197 expression in MDS69 metab and MDS69 metab low mutation rate hosts. The OmpF-CRM197 clone produces more soluble periplasmic CRM197 in the MDS69 meta low mut host (lanes 5-6) than the ompA-CRM197 clone (lanes 8-9) in the same host and using the same induction conditions. Lanes 11-15 represent samples of the medium supernatant after cell harvest and demonstrate that little to no CRM197 is released to the medium under these induction and growth conditions.

FIGS. 16A-16C depict CRM197 DNA and amino acid sequences. FIG. 16A depicts the DNA sequence of the CRM197 ORF optimized for expression with a signal sequence to direct expression and processing of the mature CRM197 protein to the periplasmic space. FIG. 16B depicts the DNA sequence of the CRM197 ORF optimized for expression in the cytoplasm. FIG. 16C depicts the amino acid sequence of the mature CRM197 protein produced after signal sequence processing (FIG. 16A) or N-terminal Methionine removal (FIG. 16B).

FIG. 17 depicts signal sequences examined in relation to periplasmic delivery of CRM197 in reduced genome strain MDS69 metab, classified according to their relative abundance in *E. coli* K and/or B strains.

FIG. 18 depicts the μg/OD (top panel) and μg/ml of periplasmic CRM197 (Caliper analysis) with the following signal sequences: OmpF, MalE, HdeA, OppA, HdeB and GlnH (Induction A) and OmpF, MglB, Agp, OmpC, RbsB, FkpA, and YtfQ (Induction B) at 25 μM inducer (IPTG) added at OD ~0.3 in reduced genome *E. coli* strain MDS69 metab.

FIG. 19 depicts the μg/OD (top panel) and μg/ml of periplasmic CRM197 (Caliper analysis) with the following signal sequences: OmpF, MalE, HdeA, OppA, HdeB and GlnH (Induction A) and OmpF, MglB, Agp, OmpC, RbsB, FkpA, and YtfQ (Induction B) at 35 μM inducer (IPTG) added at OD ~0.3 in reduced genome *E. coli* strain MDS69 metab.

FIG. 20 depicts the μg/OD (top panel) and μg/ml of periplasmic CRM197 (Caliper analysis) with the following signal sequences: OmpF, MalE, HdeA, OppA, HdeB and GlnH (Induction A) and OmpF, MglB, Agp, OmpC, RbsB, FkpA, and YtfQ (Induction B) at 50 μM inducer (IPTG) added at OD ~0.3 in reduced genome *E. coli* strain MDS69 metab.

FIG. 21 compares the μg/OD (top panel) and μg/ml of periplasmic CRM197 (Caliper analysis) obtained with the OmpF signal sequence at 0, 25 35 and 50 μM inducer and with the YtfQ signal sequence at 0, 25, 35, 50, 75, 100, 150 and 250 μM inducer added at OD ~0.3 in reduced genome *E. coli* strain MDS69 metab. The results are the average of two sets of experiments.

FIG. 22 is a protein gel analysis comparing CRM197 yield in periplasm (P) and media (M) of MDS69 metab with OmpF or YtfQ signal sequence at inducer concentration of 50 μM (OmpF) or 50, 75, 100, 150, 250 μM (YtfQ) added at OD=0.3 (late stage). Samples were collected at the specified OD for analysis.

FIG. 23 compares periplasmic expression of CRM197 in MDS metab cells with OmpF or YtfQ signal sequence and in BL21(DE3) cells with ompF signal sequence at the indicated inducer concentrations. Inducer was added at OD ~2 (very late induction) and samples were analyzed by Caliper. The g/L of (soluble) periplasmic CRM197 (extrapolated to OD600=250) is indicated at each concentration of inducer.

DETAILED DESCRIPTION OF THE INVENTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

Figure 1:
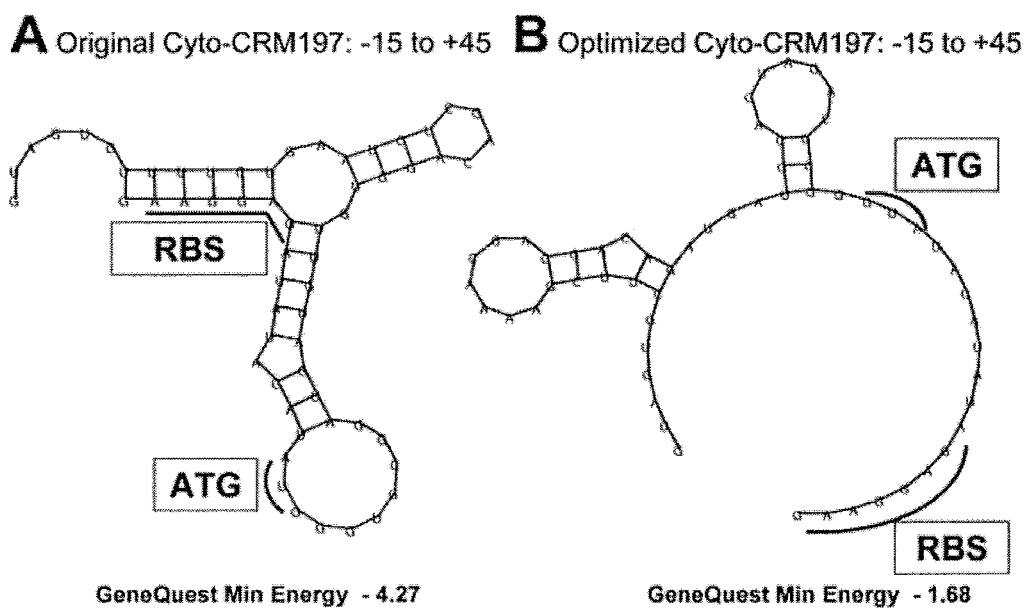
FIG. 1 depicts the DNA sequence changes that result in a release of hairpin structures in the CRM197 sequence used in experiments aimed at examining the insoluble form of CRM197. The optimized sequence (B) generates a higher minimal energy (−1.68 for the optimized sequence compared to −4.27 for the original sequence) and relaxes secondary structure enhancing recognition of both the start site (ATG) and ribosomal binding site (RBS) relative to the original sequence.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. As used herein, the terms "about" and "approximately" when referring to a numerical value shall have their plain and ordinary meanings to one skilled in the pertinent art at issue. Also, the disclosure of ranges is intended as a continuous range including every value between the minimum and maximum values recited as well as any ranges that can be formed by such values. This includes ranges that can be formed that do or do not include a finite upper and/or lower boundary. This also includes ratios that are derivable by dividing a given disclosed numeral into another disclosed numeral. Accordingly, the skilled person will appreciate that many such ratios, ranges, and ranges of ratios can be unambiguously derived from the data and numbers presented herein and all represent various embodiments of the present invention.

A "reduced genome" bacterium as used herein means a bacterium having about 1% to about 75% of its genome (e.g. protein coding genes) deleted, for example about 5%, about 10%, about 20%, about 30% about 40%, about 50% or about 60% of the genome deleted. In one embodiment, the reduced genome bacteria used in the practice of the present invention have a genome that is preferably genetically engineered to be at least two percent (2%) and up to twenty percent (20%) (including any number therebetween) smaller than the genome of a native parent strain. Preferably, the genome is at least five percent (5%) and up to thirty percent (30%) smaller than the genome of a native parent strain. More preferably, the genome is eight percent (8%) to fourteen percent (14%) to twenty percent (20%) (including any number therebetween) or more smaller than the genome of the native parent strain. Alternatively, the genome may be engineered to be less than 20%, less than 30%, less than 40% or less than 50% smaller than the genome of a native parental strain. The term "native parental strain" means a bacterial strain found in a natural or native environment as commonly understood by the scientific community to represent the foundation of a strain line and on whose genome a series of deletions can be made to generate a bacterial strain with a smaller genome. Native parent strain also refers to a strain against which the engineered strain is compared and wherein the engineered strain has less than the full complement of the native parent strain. The percentage by which a genome has become smaller after a series of deletions is calculated by dividing "the total number of base pairs deleted after all of the deletions" by "the total number of base pairs in the genome before all of the deletions" and then multiplying by 100. Similarly, the percentage by which the genome is smaller than the native parent strain is calculated by dividing the total number of nucleotides in the strain with the smaller genome (regardless of the process by which it was produced) by the total number of nucleotides in a native parent strain and then multiplying by 100.

In one embodiment, a "reduced genome" bacterium means a bacteria for which removal of the above amounts of genome does not unacceptably affect the ability of the organism to grow on minimal medium. Whether removal of two or more genes "unacceptably affects" the ability of the organism to grow on minimal medium in the present context depends on the specific application. For example, a 30% reduction in proliferation rate may be acceptable for one application but not another. In addition, adverse effect of deleting a DNA sequence from the genome may be reduced by measures such as changing culture conditions. Such measures may turn an otherwise unacceptable adverse effect to an acceptable one. In one embodiment, the proliferation rate is approximately the same as the parental strain. However, proliferation rates ranging from about 5%, 10%, 15%, 20%, 30%, 40% to about 50% lower than that of the parental strain are within the scope of the invention. More particularly, doubling times of bacteria of the present invention may range from about fifteen minutes to about three hours. Non-limiting examples of suitable reduced genome bacteria, as well as methods for deleting DNA from a bacterium such as $E.\ coli$, are disclosed in U.S. Pat. Nos. 6,989,265, 7,303,906, 8,119,365, 8,039,243 and 8,178,339, each of which is hereby incorporated by reference herein.

The term "b number" used herein refers to the unique ID assigned to each gene of the K-12 MG1655 strain as described in Blattner et al., Science 277:1453-1474 (1997).

The term "CRM197" used herein refers to cross-reacting material 197 (CRM197), a diphtheria toxin variant having a single G→A transition leading to the substitution of glycine (at position 52 in the wild-type toxin) with glutamic acid in CRM197. This missense mutation is responsible for the loss of ADP-ribosyltransferase activity. See e.g. Giannini et al., Nucleic Acids Res. 12(10):4063-4069 (1984).

In several embodiments, a method for producing a recombinant CRM197 protein in a reduced genome $E.\ coli$ host cell is provided. It has been found that a surprisingly high yield of recombinant CRM197 can be produced in insoluble or soluble form using reduced genome $E.\ coli$ host strains e.g. compared to wild type $E.\ coli$ host strains. In one aspect, the method leads to increased production of insoluble CRM197 in the cytoplasm of the host cell. In other aspects, the method leads to increased production of soluble CRM197 in the periplasm of the host cell. In preferred embodiments, the native parent $E.\ coli$ strain used to create the reduced genome $E.\ coli$ host cell is a K-12 strain such as K-12 strain MG1655.

In some embodiments, a native K-12 strain such as K-12 MG1655 is used to produce recombinant CRM197 according to the methods herein described.

The nucleotide sequence of CRM197 for use according to the present invention may be prepared using recombinant DNA technology. For example, CRM197 can be chemically synthesized or can be prepared by site-directed mutagenesis based on the known nucleotide sequence of the wild type structural gene for diphtheria toxin carried by cornyebacteriophage β (Greenfield et al., Proc Nat Acad Sci, 80:6953-6957 (1993)). Preferably, the nucleotide sequence of CRM197 is optimized for expression in $E.\ coli$.

A variety of sequence features of the heterologous nucleic acid can be optimized including, without limitation, modification of translation initiation regions, alteration of mRNA structural elements, and the use of different codon biases. Methods for optimizing nucleic acid sequence to improve expression in $E.\ coli$ host cells are known in the art and described e.g. in U.S. Pat. No. 7,561,972, the contents of which are incorporated herein by reference. Preferably, optimization of the nucleotide sequence of CRM197 for expression in *E. coli* comprises at least codon optimization. The presence of codons in the heterologous nucleic acid sequence that are rarely used in *E. coli* can delay translation of the encoded protein and result in a reduced expression in the *E. coli* host cell. Thus, in one aspect, the general codon usage in *E. coli* is used to optimize the expression of CRM197 in *E. coli*. Optimization of CRM197 for expression in *E. coli* also preferably includes minimization of interfering secondary structure. Interfering secondary structure can result in reduced expression of heterologous proteins in *E. coli* by impeding transcription and translation. For example, mRNA secondary structure at the initiation site has been inversely correlated to translational efficiency. An exemplary CRM197 nucleotide sequence, optimized for expression in the periplasm of *E. coli* when attached to an upstream region encoding a signal sequence is provided as SEQ ID NO: 1 (FIG. 16A). An exemplary CRM197 nucleotide sequence, optimized for expression in the cytoplasm of *E. coli* when attached to an upstream ATG start codon is provided as SEQ ID NO: 3 (FIG. 16B). It is to be understood that the methods of the present invention are not limited to the CRM197 nucleotide sequence set forth as SEQ ID NO: 1. Additional strategies for optimizing heterologous nucleotide sequences for expression in *E. coli* are known in the art and can be used in addition to or as an alternative to the strategies described above.

Processes for preparing recombinant heterologous proteins from genetically engineered bacterial host cells such as *E. coli* comprising expression systems are well known to those skilled in the art. Recombinant CRM197 can be expressed in (e.g. reduced genome) *E. coli* host cells by any of these methods. In one aspect, the present methods relate to reduced genome *E. coli* host cells comprising expression systems, the expression systems comprising nucleotide sequence encoding CRM197 operably linked to an inducible promoter such that CRM197 is expressed in the host cells when the promoter is induced. In a preferred aspect, the promoter is induced by addition of a suitable amount of IPTG. Introduction of a polynucleotide into the reduced genome *E. coli* host cell can be accomplished by any of several standard molecular biology techniques such as those described in Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989) including, without limitation, calcium phosphate transfection, microinjection, electroporation, conjugation, infection and the like. Similarly, any system or vector suitable to maintain, propagate or express polynucleotides and/or express a polypeptide in a host may be used to practice the present invention. For example, the appropriate DNA sequence may be inserted into a vector such as a plasmid by standard techniques.

One aspect of the invention relates to periplasmic expression of CRM197 in a (e.g. reduced genome) *E. coli* host cell. The expression of proteins in the periplasm has been used for industrial use and has been reviewed in Hanahan, J. Mol. Biol., 166:557-580 (1983); Hockney, Trends Biotechnol., 12:456-632 (1994); and Hannig et al., Trends Biotechnol., 16:54-60 (1998), each of which is incorporated herein by reference. Thus, in several embodiments, methods are provided comprising growing a (e.g. reduced genome) *E. coli* comprising an expression vector comprising a nucleic acid sequence encoding a CRM197 protein fused to a signal sequence, operably linked to an expression control sequence under conditions suitable for the expression of the recombinant CRM197 protein, wherein the signal sequence directs transfer of the CRM197 protein to the periplasm of the *E. coli* host. According to these methods, a surprisingly high yield of intact soluble CRM197 is produced and substantially all of the soluble CRM197 can be recovered.

The presence of a signal sequence on a protein facilitates the transport of the newly translated protein across the inner membrane of *E. coli* into the periplasmic space. The signal sequence is then cleaved; accordingly replacement of the native *C. diphtheriae* signal sequence with a signal sequence that directs transfer of CRM197 to the periplasm of *E. coli* ultimately results in a mature protein having the same amino acid sequence.

Representative examples of signal sequences capable of directing heterologous proteins to the *E. coli* periplasm are listed below. It is to be understood that signal sequences useful in the methods of the present invention are not limited to those listed below. Preferably, the signal sequence results in direction of at least 70, 80, 90 or 100% of the polypeptide to the periplasm when expressed in *E. coli*.

| Signal Sequence | Amino acid sequence |
|---|---|
| PelB (pectate lyase B) | MKYLLPTAAAGLLLLAAQPAMA (SEQ ID NO: 4) |
| OmpA (outer-membrane protein A) | MKKTAIAIAVALAGFATVAQA (SEQ ID NO: 5) |
| StII (heat-stable enterotoxin 2) | MKKNIAFLLASMFVFSIATNAYA (SEQ ID NO: 6) |
| Endoxylanase | MFKFKKKFLVGLTAAFMSISMFSATASA (SEQ ID NO: 7) |
| PhoA (alkaline phosphatase) | MKQSTIALALLPLLFTPVTKA (SEQ ID NO: 8) |
| OmpF (outer-membrane protein F) | MMKRNILAVIVPALLVAGTANA (SEQ ID NO: 9) |
| PhoE (outer-membrane pore protein E) | MKKSTLALVVMGIVASASVQA (SEQ ID NO: 10) |
| MalE (maltose-binding protein) | MKIKTGARILALSALTTMMFSASALA (SEQ ID NO: 11) |

-continued

| Signal Sequence | Amino acid sequence |
|---|---|
| OmpC (outer-membrane protein C) | MKVKVLSLLVPALLVAGAANA (SEQ ID NO: 12) |
| Lpp (murein lipoprotein) | MKATKLVLGAVILGSTLLAG (SEQ ID NO: 13) |
| LamB (λ receptor protein) | MMITLRKLPLAVAVAAGVMSAQAMA (SEQ ID NO: 14) |
| OmpT (protease VII) | MRAKLLGIVLTTPIAISSFA (SEQ ID NO: 15) |
| LTB (heat-labile enterotoxin subunit B) | MNKVKCYVLFTALLSSLYAHG (SEQ ID NO: 16) |
| MglB (methyl galactose transporter) | MNKKVLTLSAVMASMLFGAAAHA (SEQ ID NO: 17) |
| OppA (oligopeptide transporter) | MTNITKRSLVAAGVLAALMAGNVALA (SEQ ID NO: 18) |
| RbsB (subunit ribose transporter) | MNMKKLATLVSAVALSATVSANAMA (SEQ ID NO: 19) |
| Agp (glucose-1 phosphatase, 3-phytase)) | MNKTLIAAAVAGIVLLASNAQA (SEQ ID NO: 20) |
| FkpA (peptidyl-prolyl cis-trans isomerase) | MKSLFKVTLLATTMAVALHAPITFA (SEQ ID NO: 21) |
| YtfQ (galactofuranose binding protein, subunit ABC transporter) | MWKRLLIVSAVSAAMSSMALA (SEQ ID NO: 22) |
| HdeA (stress response induced by acidic conditions) | MKKVLGVILGGLLLLPVVSNA (SEQ ID NO: 23) |
| HdeB (stress response induced by acidic conditions) | MNISSLRKAFIFMGAVAALSLVNAQSALA (SEQ ID NO: 24) |
| GlnH (subunit of glutamine ABC transporter) | MKSVLKVSLAALTLAFAVSSHA (SEQ ID NO: 25) |

Additional signal sequences for use according to the invention include, without limitation, CpdB (3'-nucleotidease/2',3'-cyclic nucleotide 2'-phosphodiesterase), YdeN (putative sulfatase), OsmY (induced by hyperosmotic stress), ArtI (subunit Arginine ABC transporter), GltL (glutamate ABC transporter), and CybC (cytochrome b562).

In preferred embodiments, the signal sequence is selected from the ytfQ, OmpA and OmpF signal sequences. In a particularly preferred embodiment, the signal sequence is the OmpF signal sequence. In another particularly preferred embodiment, the signal sequence is the YtfQ signal sequence.

Any reduced genome E. coli strain may be used as a host cell according to the methods described herein. In one aspect, the reduced genome E. coli has a genome that is genetically engineered to be at least two percent (2%) and up to forty percent (40%) (including any number therebetween), such as between 5% and 30% or between 5% and 20%, smaller than the genome of its native parent strain. The percentage by which a genome has become smaller after a series of deletions is calculated by dividing "the total number of base pairs deleted after all of the deletions" by "the total number of base pairs in the genome of the parental strain before all of the deletions" and then multiplying by 100. In another aspect, the reduced genome bacterium has a genome that is between 4.41 Mb and 3.71 Mb, between 4.41 Mb and 3.25 Mb or between 4.41 Mb and 2.78 Mb. The reduced genome E. coli strain for use according to the methods described herein may be produced by cumulative genomic deletions of a parent E. coli strain by the methods described in International Patent Publication No. WO 2003/070880.

The parental E. coli strain may be any E. coli strain but is preferably a K-12 strain (e.g. MG1655 (ATCC No. 47076) or W3110 (ATCC No. 27325)) or B strain. A particularly preferred parental E. coli strain is K-12 strain MG1655 (annotated version m56, NCBI accession no. U000961) with a genome having 4,639,674 base pairs.

In one aspect, the parental E. coli strain is a K-12 strain lacking one or more of the genes listed at Tables 2-20 of U.S. Pat. No. 8,178,339, incorporated herein by reference. In a preferred embodiment, the reduced genome E. coli K-12 strain lacks at least the following genes (identified by "b" numbers based on the designations set out in Blattner et al., Science, 277:1453-74 and in GenBank Accession No. 400096): b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-b4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, and b4455, which are the genes deleted from *E. coli* K-12 MG1655 to create reduced genome (or multiple deletion) strain MDS39. In another preferred embodiment, the reduced genome *E. coli* K-12 strain further lacks the following gene: b1786, which is the gene deleted from MDS39 to create reduced genome strain MDS40. In another preferred embodiment, the reduced genome *E. coli* K-12 strain further lacks the following genes: b0150-b01530, which are the genes deleted from MDS40 to create MDS41 In yet another preferred embodiment, the reduced genome *E. coli* K-12 strain further lacks the following gene: b2945 (endA) which is the gene deleted from MDS41 to create reduced genome strain MDS42. In still another embodiment, the reduced genome *E. coli* K-12 strain further lacks any of the following genes: b0315-b0331, b0333-b0341 and b0346-b0354, which are the genes deleted from MDS42 to create reduced genome strain MDS43. In yet another embodiment, the reduced genome *E. coli* K-12 strain further lacks any of the following genes: b2481-b2492, b2219-b2230, b4500, b3707-b3723, b0644-b0650, b4079-4090, b4487, b4092-b4106, b0730-b0732, b3572-b3587, b1653, b2735-b2740, b2405-b2407, b3896-b3900, b1202, b4263-b4268, b0611, b2364-b2366, b0839, b0488-b0500, b0502, which are the genes deleted from MDS43 to create MDS60. In yet another preferred embodiment, the reduced genome *E. coli* K-12 strain further lacks any of the following genes: b0566-b0575, b2209, b0160-b0161, b1431-b1444, b3643, b1037-b1043, b0383, b0226-b0234, b2115-b2132, which are the genes deleted from MDS60 to create MDS69. In certain embodiments, the reduced genome *E. coli* K-12 strain for use in the methods described herein is MDS41, MDS42, MDS60 or MDS69.

*E. coli* host cells for use in the present invention preferably comprise a functional recA gene (b2699), although *E. coli* lacking a functional recA gene (b2699) can also be used as a host cell for producing CRM197. For example, a reduced genome *E. coli* strain such as e.g. strain MDS40, MDS41, MDS42 or MDS69 can be modified by inactivation of b2699 by complete or partial deletion of the gene from the modified *E. coli* K-12 strain. In one embodiment, CRM197 fused to an OmpA signal sequence is expressed in a reduced genome *E. coli* host lacking a functional recA gene.

In another aspect, the reduced genome *E. coli* comprises one or more non-functional genes selected from the group consisting of the genes encoding Pol II, Pol IV and Pol V, as described in WIPO Publication No. 2013/059595, the contents of which are incorporated herein by reference. In one embodiment, the reduced genome *E. coli* has non-functional PolB (encoded by b0060, coordinates 63429-65780 on the *E. coli* K12 MG1655 genome) and DinB (encoded by b0231, coordinates 250898-251953 on the MG1655 genome) genes. In another embodiment, the reduced genome *E. coli* has non-functional PolB, DinB and UmuDC (encoded by b1183-b1184, coordinates 1229990-1231667 on the MG1655 genome) genes. Preferably, the gene(s) are rendered inactive by complete or partial deletion. For example, the polB, dinB and umuDC genes may be rendered nonfunctional in a reduced genome *E. coli* strain such as strain MDS40, MDS41, MDS42 or MDS69.

In another aspect, the reduced genome *E. coli* (e.g. strain MDS40, MDS41, MDS42 or MDS69) has been genetically modified so as to (a) enhance orotate phosphoribosyltransferase activity (b) produce active acetohydroxy acid synthase II and (c) reduce expression of the iclR and arpA gene products.

*E. coli* orotate phosphoribosyltransferase, an enzyme that catalyzes synthesis of pyrimidine nucleotides, is encoded by the pyrE gene, b-number b3642. The pyrE gene is present in an operon with the upstream rph gene (b3643). The pyrE gene is expressed at sub-optimal levels in *E. coli* K-12 strains such as MG1655 and W3310 due to a −1 frame shift mutation in the coding region of the rph gene. Orotate phosphoribosyltransferase activity can be enhanced by a deletion that entirely removes the rph coding sequence to bring the promoter of the rph-pyrE operon closer to the translation initiation site of pyrE. Alternatively, any of the methods described in U.S. Pat. No. 8,293,505, the contents of which are incorporated by reference, can be used to enhance orotate phosphoribosyltransferase activity.

*E. coli* acetohydroxy acid synthase II normally consists of a large subunit, encoded by the ilvG gene and a small subunit, encoded by the ilvM gene (b3769). The ilvG sequence of *E. coli* K-12 strain MG1655 is corrupted and is actually a pseudo gene (b-number b4488), as set forth in GenBank Accession No. AAC77488.1. The ilvG pseudo gene is comprised of two separate coding sequences, ilvG_1 (b3767) and ilvG_2 (b3768). The ilvG pseudo gene sequence in K-12 strains such as MG1655 comprises a deletion of nucleotides GT at positions 983 and 984 relative to the intact ilvG genes found in other *E. coli* strains (e.g. B strain, O strain, etc.). The deletion of these nucleotides results in a frameshift mutation and nucleotides TGA at positions 982-984 of the K-12 ilvG pseudo gene sequence serve as a premature termination codon resulting in a truncated form of ilvG corresponding to ilvG_1. Thus, the normal gene product of ilvG is not expressed and acetohydroxy acid synthase II is not present in *E. coli* K-12 strains. The reduced genome *E. coli* can be modified to produce active acetohydroxy acid synthase II by the introduction of a mutation which complements a native −2 frameshift mutation in the ilvG gene. Alternatively, the reduced genome *E. coli* can be modified to produce active acetohydroxy acid synthase II by any of the methods of U.S. Pat. No. 7,300,776, the entire contents of which are incorporated herein by reference.

The iclR and arpA genes of *E. coli* K strain are adjacent genes encoding regulatory proteins that modulate expression of the glyoxylate shunt enzymes and of acetyl-CoA synthetase, respectively. The iclR (isocitrate lyase regulator) gene, b-number b4018, is described at NCBI Entrez GeneID No. 948524. The arpA (ankyrin-like regulator protein) gene, b-number b4017, is described at NCBI Entrez GeneID No. 944933. The arpA gene was found to be partially deleted in the genome sequence of B strains such as BL21DE3 and REL606 relative to the K-12 strain sequence. The iclR and arpA genes can be inactivated (i.e. rendered non-functional) in the reduced genome *E. coli* by deletion of all or part of the iclR and arpA gene sequences for example by the "scarless" deletion methods described at column 8, line 45 to column 14, line 41 of U.S. Pat. No. 6,989,265.

In other embodiments, the reduced genome *E. coli* comprises a relA gene containing any of the mutations described in U.S. Pat. No. 8,367,380, the contents of which are incorporated herein by reference. For example, a reduced genome *E. coli* strain such as strain MDS40, MDS41, MDS42 or MDS69 may be modified to incorporate any of these mutations.

Reduced genome *E. coli* for use according to the invention may comprise any combination of the modifications described above. In some preferred embodiments, a reduced genome *E. coli* comprising at least the deletions of MDS42 or comprises at least the deletions of MDS69 and has been genetically modified so as to (a) enhance orotate phosphoribosyltransferase activity (b) produce active acetohydroxy acid synthase II and (c) reduce expression of the iclR and arpA gene products is employed as a host for periplasmic production of CRM197. The reduced genome *E. coli* preferably comprises a functional recA gene.

Various protein coding genes can be deleted to form reduced genome bacteria. In *E. coli* and other bacteria, a type of DNA sequence that can be deleted includes those that in general will adversely affect the stability of the organism or of the gene products of that organism. Such elements that give rise to instability include without limitation transposable elements, insertion sequences, and other "selfish DNA" elements which may play a role in genome instability. For example, insertion sequence (IS) elements and their associated transposes are often found in bacterial genomes, and thus are targets for deletion. IS sequences are common in *E. coli*, and all of them may be deleted. For purposes of clarity in this document, we use the term IS element and transposable element generically to refer to DNA elements, whether intact or defective, that can move from one point to another in the genome. An example of the detrimental effects of IS elements in science and technology is the fact that they can hop from the genome of the host *E. coli* into a plasmid during propagation for sequencing. This artifact can be prevented by deletion from the host cells of all IS elements. For a specific application, other specific genes associated with genomic instability, such as active and inactive prophages may also be deleted. In particularly preferred embodiments, the reduced genome *E. coli* host according to the invention has deleted therefrom all insertion sequences (i.e. does not comprise insertion sequences). In a related aspect, the reduced genome *E. coli* host lacks all IS1, IS2, IS3, IS5, IS 150 and IS 186 insertion sequences.

Reduced genome bacteria of the invention may also be engineered to lack, for example, without limitation, certain genes unnecessary for growth and metabolism of the bacteria, pseudo genes, prophage, undesirable endogenous restriction-modification genes, pathogenicity genes, toxin genes, fimbrial genes, periplasmic protein genes, invasin genes, lipopolysaccharide genes, class III secretion systems, phage virulence determinants, phage receptors, pathogenicity islands, RHS elements, sequences of unknown function and sequences not found in common between two strains of the same native parental species of bacterium. Other DNA sequences that are not required for cell survival can also be deleted or omitted.

In a particularly preferred embodiment, a reduced genome *E. coli* is provided having a genome between five percent (5%) and thirty percent (30%) smaller than the genome of a native parent *E. coli* K strain and lacking all insertion sequence (IS) elements. Positions of the IS elements on a genome map of *E. coli* MG1655 are shown in FIG. 1 and Table 2 of U.S. Pat. No. 8,178,339, the contents of which are incorporated herein by reference. Insertion sequence elements which commonly occur in *E. coli* and which may be removed, include without limitation, IS1, IS2, IS3, IS4, IS5, IS30, IS150, IS186, IS600, IS911 and IS10. Preferably, the native parent *E. coli* strain is *E. coli* K-12 strain MG1655.

In another particularly preferred embodiment, the reduced genome *E. coli* comprises deletion(s) of one or more periplasmic protein genes, including without limitation, the following genes alone or in any combination: b0018, b0150, b0152-b0153, b0161, b0227, b0250, b0291-b0293, b0297, b0316, b0329, b0365, b0371, b0376, b0383-b0384, b0494, b0497-b0498, b0545, b0553, b0559, b0562, b0565, b0567, b0569, b0572-b0574, b0611, b0700, b0704, b0839, b0983-b0986, b1023-b1024, b1072, b1079-b1080, b1083, b1038-b1039, b1041-b1043, b1329, b1357, b1369, b1377, b1383, b1386, b1435-b1436, b1440, b1562, b1878, b1889, b1920, b1995, b2000, b2062, b2123, b2126, b2131-b2132, b2190, b2209, b2487, b2637, b2647, b2945, b3043, b3046-b3048, b3215-b3216, b3219, b3325, b3329, b3338, b3482, b3579, b3584, b3586, b3593, b3596, b4080, b4088, b4105, b4280, b4290-b4292, b4309-b4311, b4314, b4316-b4320, b4412, b4415, b4455, and b4487.

In another aspect of the invention, a native K-12 strain such as K-12 MG1655 is used to produce recombinant CRM197 according to the methods herein described.

The recombinant protein may be co-expressed with chaperones/disulfide-bond forming enzymes, which may provide proper folding of the recombinant protein, including but not limited to Skp, DnaK, DnaJ, CafIM, CafIA, DsbA, DsbB, DsbC, DsbD, PpiA, PpiD, FkpA, SurA, MBP, GST, YebF, MalE, HlyA, Hirudin, OmpF, Spy, YccA; and PspA. Nucleic acid sequences of such proteins useful for periplasmic expression of recombinant protein include, without limitation, those described in U.S. Pat. Nos. 5,747,662; 5,578,464 and 6,022,952, each of which is incorporated herein by reference.

*E. coli* host cells (reduced genome or native K12 strain) transformed with an expression vector encoding CRM197 can be cultured in any fermentation format. For example, shake flask cultures, batch, fed-batch, semi-continuous and continuous fermentation modes may be used herein. As used herein "fermentation" includes both embodiments in which literal fermentation is employed and embodiments in which other non-fermentative culture modes are employed. Further, any scale of fermentation may be employed including 1 liter scale and larger fermentation volumes. In one embodiment, the fermentation volume is or is at least 1 Liter. In other embodiments, the fermentation volume is or is at least 5 Liters, 10 Liters, 15 Liters, 20 Liters, 25 Liters, 50 Liters, 75 Liters, 100 Liters, 200 Liters, 500 Liters, 1,000 Liters, 5,000 Liters, 10,000 Liters, 50,000 Liters, or more.

In various embodiments, fermentation medium may be selected from among rich media, minimal media and mineral salts media. In preferred embodiments, a minimal medium or mineral salts medium is selected. The media is preferably free or substantially free of serum and animal-derived products. A mineral salts medium typically consists of mineral salts and a carbon source (e.g. glucose, sucrose, or glycerol). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. No organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A preferred mineral salts medium will contain glucose as the carbon source. In comparison to mineral salts media, minimal media can also contain mineral salts and a carbon source, but can be supplemented with, e.g., low levels of amino acids, vitamins, peptones, or other ingredients, though these are added at very minimal levels.

In embodiments, a target culture cell density is reached at which time an inducer, preferably IPTG, is added to initiate protein production. It is understood that the cell density at induction, the concentration of inducer, pH and temperature can be varied to determine optimal conditions for expression In preferred embodiments, the pH of the culture is from about 6.5 to 7.5.

Growth, culturing and/or fermentation of the transformed reduced genome *E. coli* is performed within a temperature range permitting survival but is preferably from about 20° C. to about 30° C., more preferably is about 25° C. In another preferred embodiment, the culturing comprises a relatively short initial incubation at 37° C. (e.g. 1 to 3 hours) and is followed by growth at about 20° C. to about 30° C., preferably about 25° C. prior to and subsequent to induction. In other embodiments, culturing comprises growth at about 25° C. prior to and subsequent to induction.

In embodiments, under shake flask conditions, inducer is added at an optical density (OD) at 600 nm of about 0.1 to about 1.5, more preferably about 0.2 to about 0.9, even more preferably about 0.3 to about 0.6) at an incubation temperature of 20-30° C., preferably 25° C. At 600 nm, 1 OD unit corresponds to about $0.8 \times 10^9$ cells/ml. In other embodiments, under fermentation conditions, inducer is added at an OD600 of about 100 to 400, more preferably about 150 to 300, most preferably between 230 and 250.

The present methods provide for an increase in the level of properly processed CRM197 in comparison with conventional expression systems, such as in wild type *E. coli* B strains. In certain embodiments, the methods provide for an increase in soluble CRM197. In this context, the term "soluble" means that the protein is not precipitated at centrifugation between approximately 5,000 and 20,000× gravity when spun for 10-30 minutes in a buffer under physiological conditions. Conversely, "insoluble" means that the protein can be precipitated by centrifugation at between 5,000 and 20,000× gravity when spun for 10-30 minutes in a buffer under physiological conditions.

The methods of the present invention can comprise recovery of recombinant CRM197 produced from the (e.g. reduced genome) *E. coli* host cells. When produced in the periplasm as a soluble protein, the recovery of recombinant CRM197 in soluble form is preferably accomplished by mechanically lysing the *E. coli* host cells in the absence of detergents and solubilizers. Mechanical disruption typically involves sonication (Neppiras and Hughes, Biotechnology and Bioengineering, 6:247-270 (1964)), microfluidization (Sauer et al., Biotechnology and Bioengineering, 33:1330-1342 (1989)), or bead milling (Limon-Lason et al., Biotechnology and Bioengineering, 21(5):745-774 (1979)). Other mechanical methods known in the art may also be employed.

Recombinant CRM197 may be purified by standard techniques known in the art including, but not limited to, ammonium sulfate or ethanol precipitation, acid extraction, anion or cation exchange chromatography, phosphocellulose chromatography, hydrophobic interaction chromatography, affinity chromatography, hydroxyapatite chromatography, immunopurification methods and the like. In a preferred embodiment, purification of recombinant CRM197 comprises hydrophobic interaction chromatography and/or anion exchange chromatography.

The yield of CRM197 can be determined by methods known to those skilled in the art such as capillary gel electrophoresis and Western blot analysis. Activity assays can also provide information regarding protein yield. Useful measures of protein yield include the amount of recombinant protein per culture volume (e.g. grams of protein/liter of culture), percent or fraction of active protein (e.g. amount of active protein/amount of protein used in the assay), percent or fraction of total cell protein, amount of protein/cell and percent or proportion of dry biomass.

Activity assays for evaluating CRM197 are known in the art and described in the literature and may include immunological assays, e.g. Western Blot analysis and ELISA, as well as receptor binding assays, e.g. Diphtheria toxin receptor (proHB-EGF) binding. In one embodiment, activity is represented by the % active recombinant CRM197 protein in the extract supernatant as compared with the total amount assayed (i.e. based on the amount of CRM197 determined to be active by the assay relative to the total amount of CRM197 used in the assay). In another embodiment, activity is represented by the % active recombinant CRM197 protein in the extract supernatant compared to a standard e.g. native protein (i.e. based on the amount of active CRM197 protein in the supernatant extract sample relative to the amount of active protein in a standard sample where the same amount of protein from each sample is used in the assay). In embodiments, about 60% to about 100%, about 70% to about 100%, about 80% to about 100%, about 90% to about 100%, about 95% to about 100%, or about 99% to about 100% of the recombinant CRM197 protein is determined to be active.

Means of confirming the identity of CRM197 are also known in the art, e.g. a protein can be analyzed by peptide mass fingerprint using MALDI-TOF mass spectrometry, N-terminal sequencing analysis or peptide mapping.

The following are among preferred embodiments of the invention

A method for producing a recombinant CRM197 in a reduced genome *E. coli* K12 strain host comprising incubating a reduced genome *E. coli* K12 strain comprising an expression vector comprising a nucleotide sequence encoding a CRM197 protein fused to a nucleotide sequence encoding OmpF or YtfQ signal sequence that directs transfer of the CRM197 protein to the periplasm of the reduced genome *E. coli* host operably linked to an expression control sequence, under conditions suitable for the expression of the recombinant CRM197 protein, whereby a yield of at least 1 gram, preferably at least 2 grams per liter of soluble CRM197 is obtained and wherein the incubation conditions comprise culturing the *E. coli* host cell in a minimal medium free of animal serum or other animal by-products.

A method for producing a recombinant CRM197 in a reduced genome *E. coli* K12 strain host comprising incubating a reduced genome *E. coli* K12 strain comprising an expression vector comprising a nucleotide sequence encoding a CRM197 protein fused to a nucleotide sequence encoding OmpF or YtfQ signal sequence that directs transfer of the CRM197 protein to the periplasm of the reduced genome *E. coli* host, operably linked to an expression control sequence under conditions suitable for the expression of the recombinant CRM197 protein, whereby a yield of at least 1 gram, preferably at least 2 grams per liter of soluble CRM197 is obtained, wherein the reduced genome *E. coli* K12 strain has deleted therefrom at least the following DNA segments: b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153 and b2945 of the *E. coli* K-12 strain MG1655 and optionally has the following additional modifications: (i) deletion of b4017, b4018 and b3643 and (ii) insertion of an AT dinucleotide at position 982 of b4488 and wherein the incubation conditions comprise culturing the E. coli host cell in a minimal medium free of animal serum or other animal by-products.

A method for producing a recombinant CRM197 in a reduced genome E. coli K12 strain host comprising incubating a reduced genome E. coli K12 strain comprising an expression vector comprising a nucleotide sequence encoding a CRM197 protein fused to a nucleotide sequence encoding OmpF or YtfQ signal sequence that directs transfer of the CRM197 protein to the periplasm of the reduced genome E. coli host, operably linked to an expression control sequence under conditions suitable for the expression of the recombinant CRM197 protein, whereby a yield of at least 1 gram, preferably at least 2 grams per liter of soluble CRM197 is obtained, wherein the reduced genome E. coli K12 strain has deleted therefrom at least the following DNA segments: b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-b4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153, b2945, b0315-b0331, b0333-b0341, b0346-b0354, b2481-b2492, b2219-b2230, b4500, b3707-b3723, b0644-b0650, b4079-4090, b4487, b4092-b4106, b0730-b0732, b3572-b3587, b1653, b2735-b2740, b2405-b2407, b3896-b3900, b1202, b4263-b4268, b0611, b2364-b2366, b0839, b0488-b0500, and b0502 of the E. coli K-12 strain MG1655 and optionally has the following additional modifications: (i) deletion of b4017, b4018 and b3643 and (ii) insertion of an AT dinucleotide at position 982 of b4488 and wherein the incubation conditions comprise culturing the E. coli host cell in a minimal medium free of animal serum or other animal by-products.

EXAMPLE 1

Cytoplasmic Expression of Insoluble CRM197 in Reduced Genome E. coli Hosts

Figure 2:
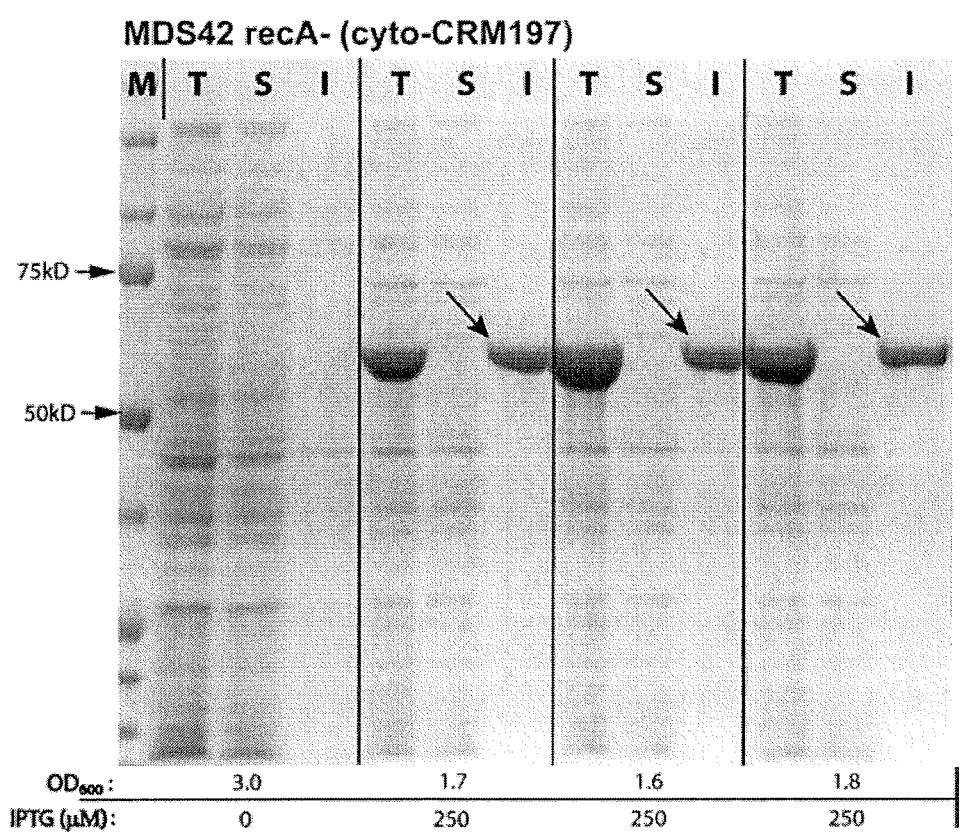
FIG. 2 depicts cytosolic expression of CRM197 in reduced genome *E. coli* strain MDS42 recA (MDS42 strain with a recA deletion). Shake flask cultures were grown in minimal media to an optical density (OD) of 0.5 and then induced with either 0 or 250 µM IPTG as indicated. Electrophoresis was with a 4-12% gradient acrylamide Bis-Tris gel

CRM197 is currently manufactured by fermentation of Corynebacterium diphtheriae C7, where it is expressed from multiple lysogens of the β phage, or from a recombinant plasmid system in Pseudomonas fluorescens. The yield of CRM197 in C. diphtheriae is low (at most ~200 mg/L) and requires biosafety level 2 (BSL2) facilities. Production in *P. flurescens* results in a higher yield (about 2 g/L); however, both hosts retain numerous mobile elements, cyrptic prophages and gene remnants with pathogenic functions. In bacterial fermentations, mobility of insertion sequence (IS) elements can lead to insertions that inactivate the gene of interest. The end result can be fermentation failure or the unwanted expression of a truncated product, both of which are economically problematic and potentially dangerous. In addition, reversion of CRM197 into its toxic parent could have disastrous consequences. Reversion of CRM197 may have contributed to toxic activity that was detected in tissue culture cells (Qiao et al., 2008). Thus, expressions systems with reduced mutation rates may provide the highest reliability and productivity coupled with the lowest level of risk for reversion.

The single greatest factor contributing to the high price and short supply of CRM197 is the historical inability to generate high amounts of CRM197 in the production workhorse *E. coli*. CRM197 is insoluble when expressed in the cytoplasm of bacteria and requires re-folding prior to use when made in standard commercial *E. coli* strains. Since relatively low amounts of CRM197 are produced in conventional strains, a reduced genome *E. coli* strain, MDS42, was tested as a production host for insoluble CRM197 in shake flask culture.

Reduced genome strain MDS42 was produced by the methods described in International Patent Publication No. WO 2003/070880, which is incorporated herein by reference. Briefly, a series of reduced genome strains (MDS01-MDS39), were produced by making a series of 39 cumulative deletions (approximately 14.1% of the genome) of nucleic acid sequences from the parental strain *E. coli* MG1655. Hybridization to genome scanning chips (NimbleGen Systems, Madison, Wis.) containing the K-12 sequence and all sequences in the IS database revealed that MDS39, the first strain designed to lack all IS elements, unexpectedly contained additional copies of an IS element that had translocated to new locations during its production. These IS elements were deleted to produce MDS40. The fhuACDB (the tonA locus) was deleted from MDS40 to produce MDS41. The location and function of each cumulative deletion made to produce MDS01-MDS41 can be found at Table 2 of U.S. Pat. No. 8,178,339, the entire content of which is incorporated herein by reference. The endA gene was then deleted from MDS41 to produce MDS42. Twenty-seven additional nucleic acid deletions were made in MDS42 to create MDS69. MDS42 and all strains based on MDS42 (MDS43, MDS44 . . . MDS69 etc.) are free of insertion sequences.

For production of insoluble CRM197, a modified CRM197 sequence was employed comprising DNA sequence changes that result in a release of hairpin structures in the CRM197 sequence. The optimized CRM197 sequence removes secondary structure that inhibits translation initiation and enhances recognition of both the start site (ATG) and ribosomal binding site (RBS). See FIG. 1.

The native CRM197 signal sequence was removed and the optimized CRM197 sequence (cyto-CRM197, SEQ ID NO: 3) amplified by PCR andsubcloned into expression vector pSX2, which contains a Kanamycin resistance cassette and uses a lactose-inducible promoter to drive expression of the cloned sequences. Plasmid pSX2 containing CRM197 (lacking its native signal sequence) was transformed into reduced genome *E. coli* strain MDS42 and examined in shake flask culture. Briefly, 3 ml cultures were grown to saturation in Korz minimal medium (Korz D J et al., J. Biotechnol., 39(1):59-65 (1995)) supplemented with 0.2% glucose and 50 μg/ml Kanamycin and used to inoculate 20 ml cultures to an initial $OD_{600}$=0.075. The growth temperature and inducer (IPTG) concentration that produced optimal levels of insoluble cytoplasmic CRM197 were then determined (in minimal media supplemented with the plasmid-selectable antibiotic kanamycin) using shake flasks. The optimal IPTG concentration was determined to be 250 μM. FIG. 2 is an example of a protein gel analyzing total cell protein (T) and the soluble fraction (S) and insoluble fraction (I) following high speed centrifugation of total cell protein from three separate cultures grown to an $OD_{600}$ of 0.5 (late induction) prior to the addition of IPTG. Surprisingly high amounts of cyto-CRM197 were present in the insoluble fractions (see FIG. 2, arrows). When quantified against protein standards, the shake flask results predict 10 to 12 g/L of cyto-CRM197 in a modest fermentation of $OD_{600}$ of 200. Production of insoluble CRM197 in the reduced genome *E. coli* host cell was 10 times higher than in conventional *E. coli* strains.

EXAMPLE 2

Periplasmic Expression of Soluble CRM197 in Reduced Genome *E. coli* Hosts

Figure 3:
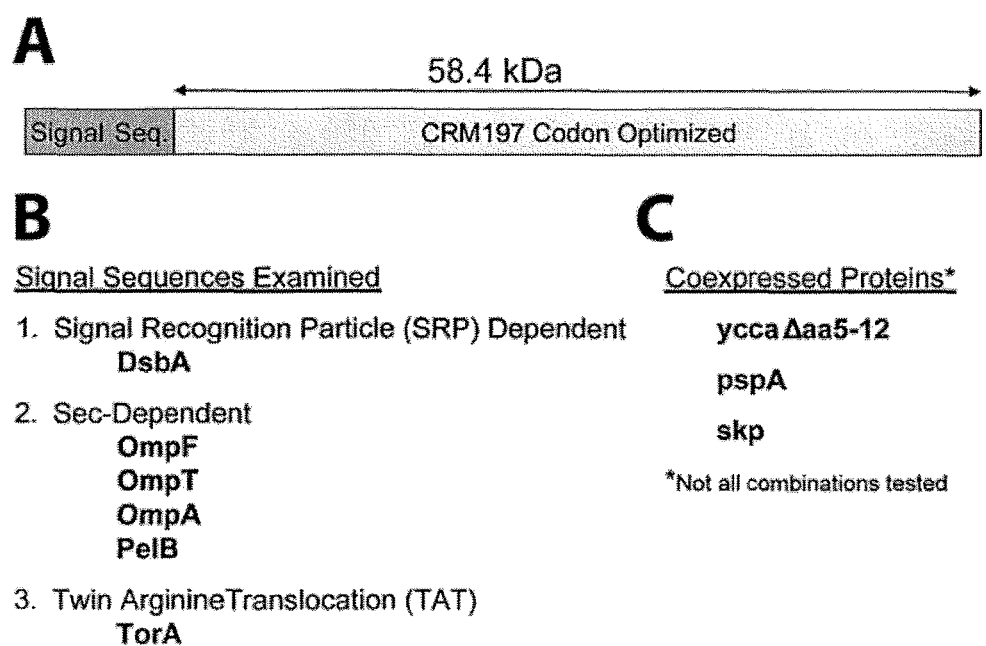

Next, production of soluble CRM197 in reduced genome *E. coli* strains was tested by directing expression of CRM197 to the periplasmic space. CRM197 has proved notoriously difficult to produce in a soluble form in *E. coli*. Export of highly expressed proteins to the periplasmic space aids stability by providing an optimal non-reducing environment for correct protein folding and formation of disulfide bridges. To this end, six signal sequences, in combination with a number of co-expressed chaperone proteins were examined to identify the signal sequence and chaperone protein that conferred the highest levels of periplasmic delivery of CRM197. FIG. 3 illustrates the signal sequences examined and the co-expressed chaperone proteins. The signal sequences examined included representative signal sequences from each of the three *E. coli* secretion pathways The CRM197 open reading frame (ORF), codon-optimized for *E. coli* (SEQ ID NO: 1), was ordered from DNA 2.0 (Menlo Park, Calif.). The CRM197 ORF was preceded by a sequence encoding a PelB signal sequence. The pelB and CRM197 ORF were flanked by sequences designed to facilitate cloning into the pSX2 expression vector. The nucleotide sequence of the 5' flanking sequence-PelB signal sequence-CRM197 ORF (including stop codon)-3' flanking sequence is provided at Table 1 below, with the flanking sequences underlined, the nucleotide sequence encoding the PelB signal sequence in bold, and the CRM197 ORF in plain text.

TABLE 1 pelB (bold)-CRM197 nucleotide sequence
(plain text) + flanking sequences (underlined):

CCTCTAGAAATAATTTTGTTTAACTTTTGAAGGAGATATACAT**ATGAA
ATACTTGCTGCCAACCGCCGCCGCCGGCCTGCTGCTGCTCGCAGCACA
GCCGGCTATGGC**AGGTGCGGATGATGTTGTGGACAGCTCTAAGTCTTT
TGTGATGGAAAACTTTAGCTCGTACCACGGTACGAAGCCAGGTTATGT
CGACAGCATTCAAAAAGGTATCCAGAAACCGAAGTCCGGCACGCAGGG
TAACTACGACGACGATTGGAAAGAGTTCTACAGCACCGACAACAAGTA
TGACGCAGCGGGTTACAGCGTTGACAATGAGAATCCGTTGAGCGGCAA
AGCGGGTGGTGTTGTCAAAGTGACGTATCCGGGTCTGACCAAGGTCCT
GGCGTTGAAAGTTGATAACGCGGAAACCATTAAGAAAGAGCTGGGTCT
GAGCCTGACCGAGCCGTTGATGGAGCAAGTTGGTACCGAAGAGTTTAT
CAAACGTTTCGGCGATGGTGCGAGCCGCGTTGTCCTGTCCCTGCCTTT
CGCGGAGGGCAGCTCCAGCGTTGAGTATATCAATAACTGGGAGCAAGC
AAAAGCGCTGTCCGTCGAACTGGAAATCAATTTTGAAACGCGCGGTAA
ACGTGGTCAAGATGCAATGTACGAGTATATGGCCCAGGCCTGCGCTGG
TAATCGTGTTCGTCGCAGCGTTGGTAGCAGCTTGCTTGCTTGTATCAACCT
GGATTGGGATGTGATCCGTGATAAGACCAAGACTAAGATCGAGAGCCT
GAAAGAACATGCCCGATTAAGAACAAGATGTCGGAGAGCCCGAATAA
GACCGTGAGCGAAGAAAAGGCCAAGCAGTATCTGGAAGAGTTCCACCA
AACGGCTCTGGAGCATCCGGAGCTGAGCGAGCTGAAAACGGTTACGGG
CACCAACCCGGTGTTCGCAGGTGCGAATTACGCGGCGTGGGCAGTGAA
TGTGGCGCAGGTCATCGACTCCGAAACGGCGGACAATTTGGAGAAAAC
CACCGCAGCGCTGAGCATTCTGCCGGGCATCGGCAGCGTTATGGGCAT
TGCAGATGGTGCTGTGCACCATAACACTGAAGAAATCGTAGCGCAAAG
CATTGCCCTGTCTAGCTTGATGGTGGCGCAGGCTATTCCGCTGGTCGG

TABLE 1-continued pelB (bold)-CRM197 nucleotide sequence
(plain text) + flanking sequences (under Completed signal sequence-CRM197 PCR products were cloned into the pSX2 expression vector. The termini of the signal sequence-CRM197 PCR products possessed 15 bp of sequence that overlaps the sequence of the pSX2 vector. The pSX2 vector was linearized with the restriction enzymes Kpn I and Sac I to facilitate the cloning reaction. Cloning reactions were transformed into MDS42, MDS42recA or MDS42recA with a further deletion of IS609, to generate recombinant pSX2 expression vectors. The signal sequence-CRM197 region and flanking vector sequences were verified by sequence analysis.

Plasmid pSX2 containing the combinations of signal sequence and CRM197 sequence (lacking its native signal sequence) illustrated at FIG. 3 (B) were transformed into reduced genome E. coli strain MDS42 or MDS42recA (MDS42 strain with a deletion of the recA gene (the recA1819 allele)) and examined in shake flask culture. In addition to signal sequence and chaperone protein, culture variables examined included temperature, inducer (IPTG) concentration and time point at which the inducer was added (either early [$OD_{600nm}$ of 0.01] or late [$OD_{600nm}$ of about 0.4]). The following conditions were determined to be optimal for periplasmic secretion of CRM197 and these conditions were used in subsequent experiments: (i) a growth temperature of about 25° C. preceded by a brief 37° C. incubation (e.g. 2 hours) (ii) late induction (addition of IPTG at an $OD_{600}$ of about 0.4) and (iii) an inducer (IPTG) concentration between 15 and 35 µM (about ⅒ that required for optimal expression of cyto-CRM197).

Briefly, 3 ml cultures were grown to saturation in Korz minimal medium supplemented with 0.2% glucose and 50 µg/ml Kanamycin and used to inoculate 20 ml cultures to an initial $OD_{600}$=0.075. The 20 ml cultures (in 125 ml baffled Erlenmeyer flasks) were placed into a 37° C. shaking incubator (250 rpm) for 2 hours. The cultures were then shifted to a 25° C. shaking incubator and monitored until $OD_{600}$ was between 0.3-0.4. At that time, IPTG was added at the indicated concentrations. The induced cultures were incubated overnight in the 25 C shaking incubator. Total induction time was between 18-22 hours. After induction, the $OD_{600}$ of the cultures was determined. Aliquots of the culture representing 2 OD units were processed to create periplasmic samples. The periplasmic samples were prepared with the aid of Periplasting Buffer (Epicentre, Madison, Wis.). The 2 OD sample was harvested by centrifugation at 7500× g for 10 minutes in a 1.5 ml Eppendorf tube. The supernatant was removed and the cell pellet gently resuspended in 50 µl of Periplasting Buffer (200 mM Tris-HCl [pH 7.5], 20% sucrose, 1 mM EDTA, and 30 U/µl Ready-Lyse Lysozyme). After 5 minutes at room temperature, 50 µl of ice cold water was rapidly added to the resuspended pellet. The mixture was incubated on ice for 5 minutes prior to fractionating the periplasmic fraction from the spheroplasts by centrifuging at 4000× g for 15 minutes. The supernatant representing the periplasmic fraction was prepared for SDS-PAGE analysis. An amount equivalent to 0.12 OD units was loaded per lane.

Figure 4:
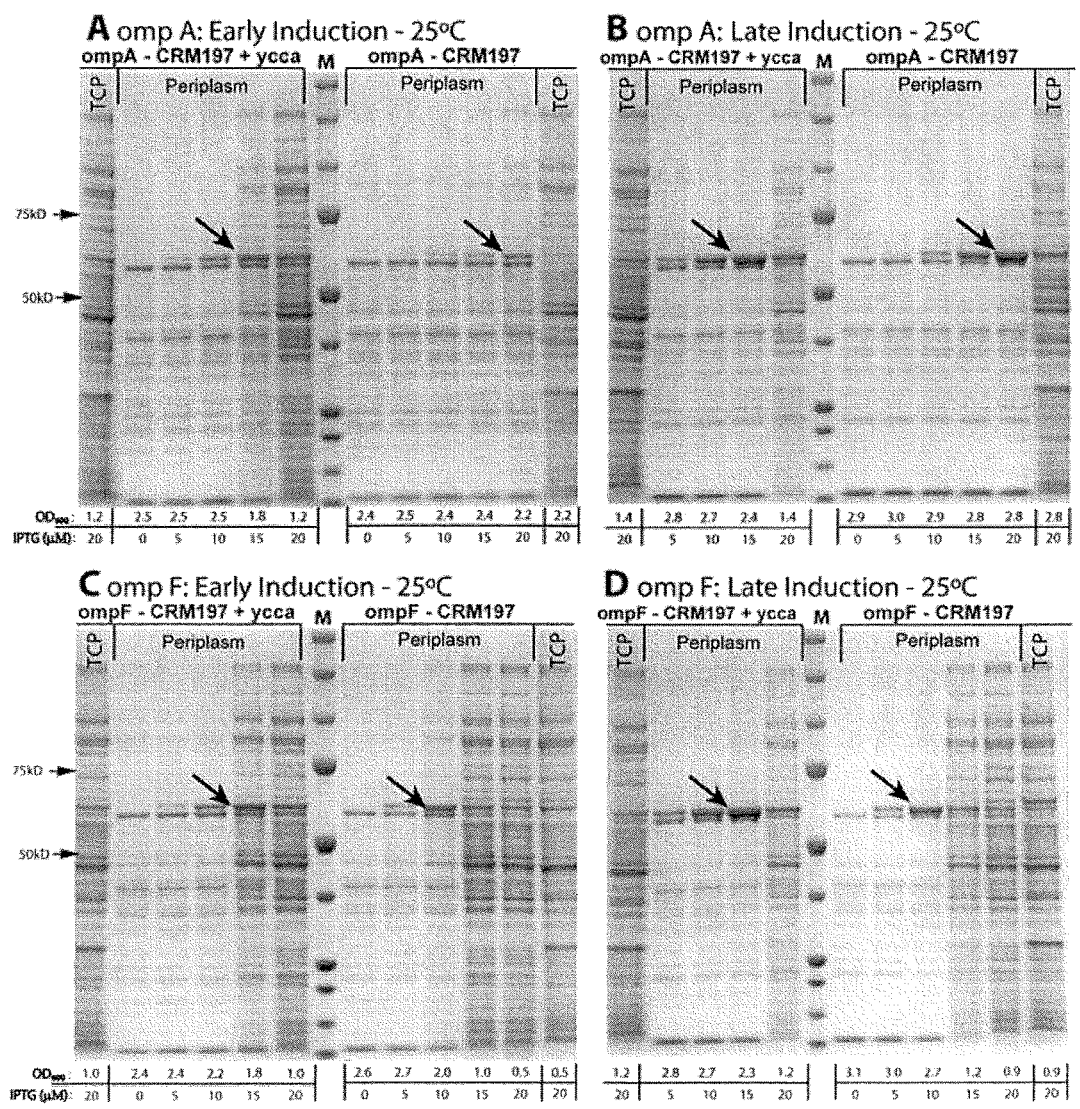
Figure 5:
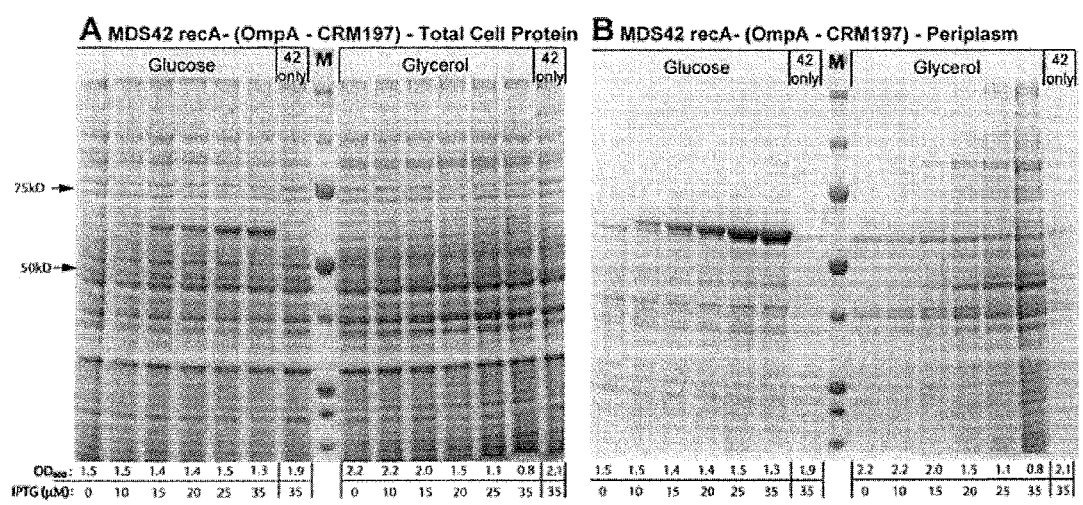
Figure 6:
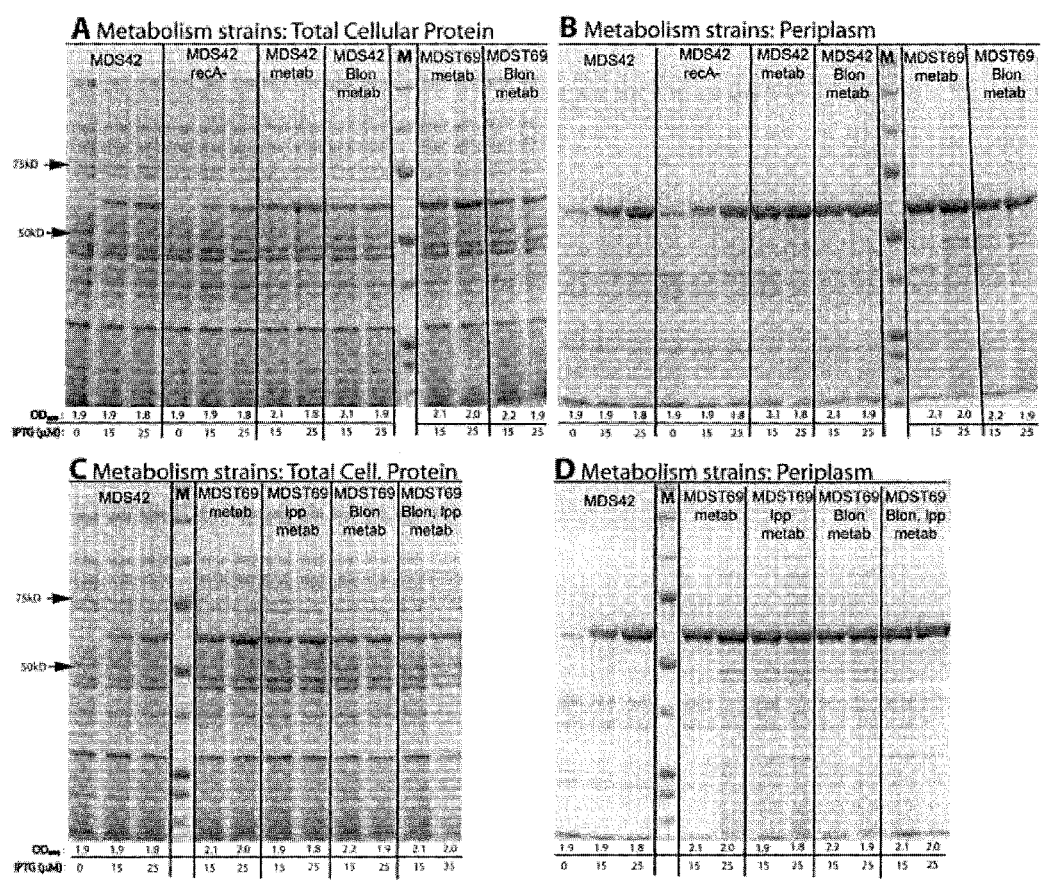

The most successful signal sequences and induction characteristics that resulted in the highest secretion of CRM197 into the periplasm are shown in FIG. 4. The periplasmic signals OmpA and OmpF were found to facilitate the greatest movement of CRM197 into the periplasm. None of the three co-expressed chaperone proteins influenced periplasmic delivery differently (as an example expression is compared with and without, YccA in FIG. 4). Since OmpA and OmpF appeared to result in roughly similar amounts of periplasmic CRM197, OmpA-CRM197 was used in subsequent experiments.

Since expression of components of the sec-dependent pathway that include ompA and ompF can be subject to catabolite repression, the influence of glycerol as a carbon source for production of ompA-CRM197 was compared to glucose in reduced genome *E. coli* strain MDS42 in shake flask cultures under the conditions described above. As illustrated at FIG. 5, minimal media supplemented with glycerol resulted in dramatically lower levels of CRM197 expression compared to glucose. Glucose was therefore used as a carbon source in all subsequent experiments.

Next, the production of periplasmic CRM197 in several different reduced genome *E. coli* host cells was compared. Thus, a series of deletions within either the MDS42 or MDS69 strain background were examined for their effect on production of periplasmic (soluble) CRM197 in shake flask cultures based on the optimal conditions described above for MDS42 that contained either (i) deletions that optimized cell metabolism or (ii) deletions that remove or reduce the level of proteases (e.g. Blon) that could adversely influence CRM197 expression. The following reduced genome *E. coli* strains based on MDS42 were tested: MDS42recA, MDS42metab, and MDS42Blon/metab. MDS42metab was created by (i) deleting the iclR (b-number b4018, described at NCBI Entrez GeneID No. 948524) and arpA genes (b-number b4017, described at NCBI Entrez GeneID No. 944933) (ii) deleting the rph gene (b3643) (thereby increasing transcriptional levels of the downstream pyrE gene), and (iii) correcting the ilvG frameshift mutation by insertion of an AT dinucleotide at position 982 (resulting in expression of active acetohydroxy acid synthase II). MDS42Blon/metab contains the modifications described for MDS42metab as well as a modification of the lon protease (b0439) promoter region to mimic the sequence of the lon promoter region of B strain *E. coli*, in which an IS insertion separates the −35 region from the −10 region of the ancestral *E. coli* ion promoter. The following reduced genome *E. coli* strains based on MDS69 were tested: MDS69metab (MDS69 strain modified as described above for MDS42metab), MDS69Blon/metab (MDS69metab further altered to include the Blon protease modification, MDS69lpp/metab (MDS69metab further modified to delete lipoprotein lpp (b1677), and MDS69Blon/lpp/metab (MDS69metab further modified to include both the Blon protease modification and lipoprotein lpp gene deletion).

FIG. 6 compares OmpA-CRM197 expression in these strains. Of the eight strains examined, the highest levels of CRM197 expression were evident in those strains (on either MDS42 or MDS69 backgrounds) that contained deletions aimed at enhancing metabolic activity (metabolism strains). However, all strains tested contained a surprisingly large amount of periplasmic CRM197 (FIG. 6 panels B and D) that was also evident on protein gels in total cellular protein preparations (FIG. 6 panels A and C). Importantly, these results indicate that the protease deletion Blon did not influence CRM197 levels in the metabolism strains. In addition, removal of the highly abundant lipoprotein protein Lpp, thought, by its absence, to "free up" the sec-dependent periplasmic transport system was also not found to influence periplasmic CRM197 levels. The media from these experiments was isolated post-induction and examined for CRM197 release. CRM197 was not identified in media from any of the strains examined. Table 2 is a summary of yield results for the MDS strains that generated the highest periplasmic CRM197 expression levels. These results were obtained by comparing stain intensities of CRM197 from the four strains indicated with protein standards run on the same gel. The shake flask values were extrapolated to predict quantities of CRM197 in fermentations that reach either 100 or 200 $OD_{600}$. The four strains shown in Table 2 typically reach ODs of 300 in fed-batch fermentation suggesting that these strains have the capacity for generating far more CRM197 than is currently possible in conventional strains.

TABLE 2

| Expression Strain with pSX2-ompA CRM197 | Periplasmic Samples | #ODs loaded | Calibrated Volume ngs/lane | % Target Protein in Periplasm | AVG g/L at 100 ODs | AVG g/L at 200 ODs |
|---|---|---|---|---|---|---|
| MDS42 Metabolism | Peri, Late 25 μM IPTG, 25° C. o/n | 0.06 0.03 | 1102 499 | 48% 53% | 1.75 | 3.5 |
| MDS69 Metabolism | Peri, Late 25 μM IPTG, 25° C. o/n | 0.06 0.03 | 1047 449 | 43% 46% | 1.62 | 3.24 |
| MDS42 Δprotease | Peri, Late 35 μM IPTG, 25° C. o/n | 0.06 0.03 | 825 330 | 47% 45% | 1.24 | 2.48 |
| MDS69 Δprotease | Peri, Late 25 μM IPTG, 25° C. o/n | 0.06 0.03 | 1028 506 | 28% 30% | 1.7 | 3.4 |

Figure 7:
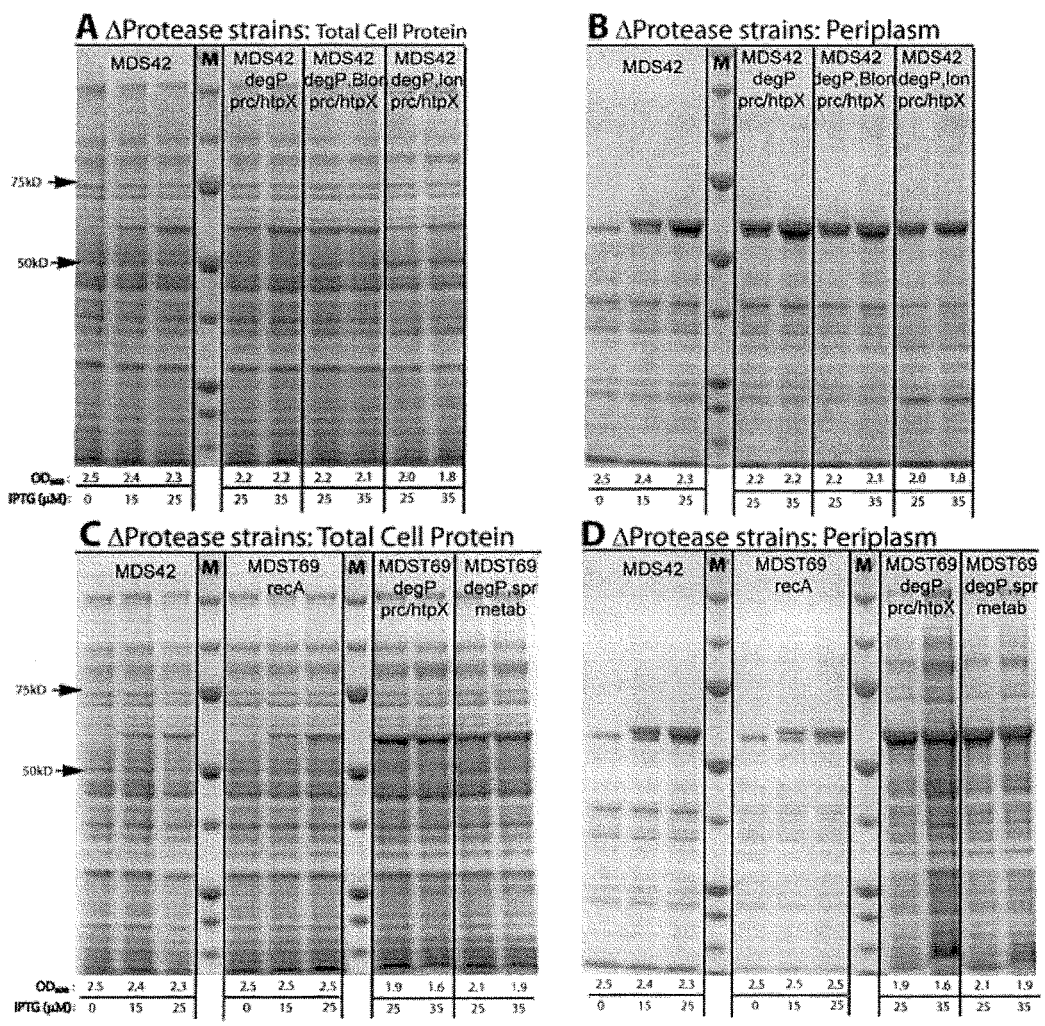

CRM197 is highly sensitive to proteolytic cleavage which has rendered production of high quality CRM197 challenging (Bishai et al., J. Bacteriol., 169:5140-51 (1987); Recombinant Production of Carrier Proteins, GEN News, Dec. 1, 2012). In a separate set of experiments, production of periplasmic CRM197 was examined in a series of protease deletion strains to determine whether the targeted removal of protease genes from the reduced genome *E. coli* strains would result in an increase in CRM197 in the periplasm. Thus, the following protease encoding genes were deleted separately in combination: degP (b0161), prc (b1830), htpX (b1829), as well as portions of the lon promoter region. Deletion of the protease genes, either individually or in combination, did not influence CRM197 expression levels. See FIG. 7, illustrating that reduced genome *E. coli* strain MDS42, modified to delete the specified combination of protease genes, had no effect on periplasmic expression of CRM197. This data indicate that proteolytic cleavage of CRM197 does not occur when produced in reduced genome *E. coli* strains based on MDS42 or MDS69 presumably due to the low levels of protease activity in these strains.

EXAMPLE 3

CRM197 Production in Fed-Batch Fermentation

Next, commercial scale-up of CRM197 in reduced genome *E. coli* strains was examined. Thus, OmpA-CRM197 in the MDS42 metabolism strain was subjected to fed-batch fermentation in defined minimal media at the 10 liter scale. Fermentation conditions included a batch phase at 37° C. that was inoculated to 0.18 OD and allowed to grow until the 1% glucose in the batch medium has been consumed (~7.5 hrs). The fed batch phase was triggered by the DO spike that occurs when the batch medium is depleted of glucose. The feed began with an exponential feed rate to produce a growth rate of 0.3 Mu (1/h) controlled gravimetrically (~12.5 hrs). The induction point was determined to be the point at which the available phosphate was nearly depleted. At a point around 2 hours prior to the induction point, the temperature was shifted to 25° C. and the feed rate was lowered to a rate that produces a growth rate of 0.2 Mu (1/hr). Once the inducer is added (100 uM) the feed was changed to a constant rate such that 80 g of glucose is added per hour for about 7 hrs. The fermentation $OD_{600}$ approached 300 and generated a very high level of periplasmic targeted CRM197 as illustrated at FIG. 8. A second fermentation at the optimal conditions resulted in periplasmic CRM197 levels of about 2 g/L indicating a high level of consistency in test fermentations.

The results described above demonstrate the surprising yield of soluble CRM197 obtained in reduced genome *E. coli* production hosts such as MDS42 and MDS69 in both shake-flask and 10 L fed-batch fermentation.

Figure 9:
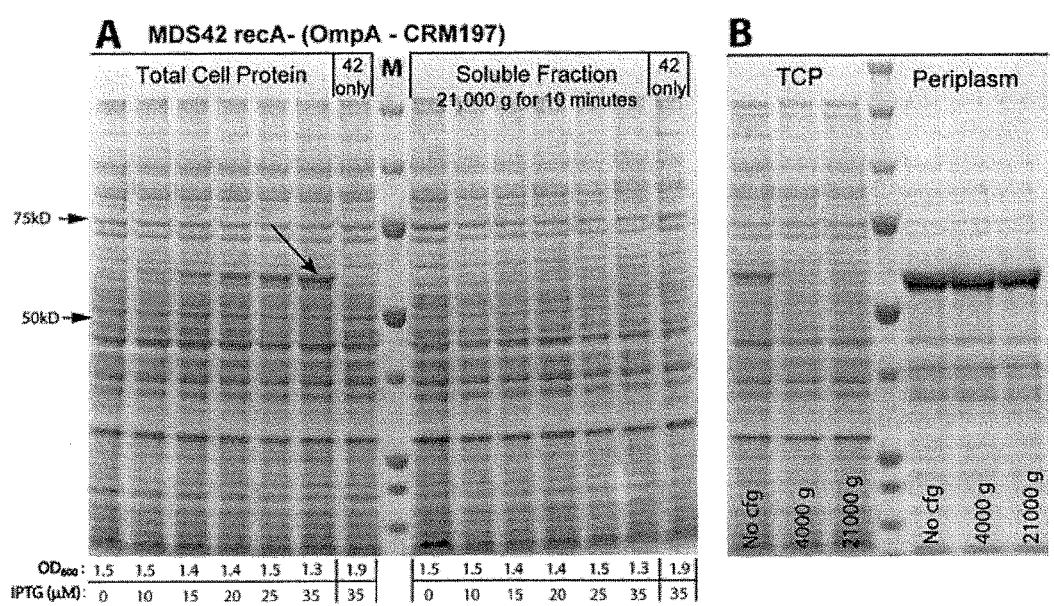

One problem observed during preliminary fermentation analysis was a reduction in the soluble form of CRM197 in total cell protein isolations. Since periplasmic isolation methods are not applicable to large scale, a general method of soluble CRM197 isolation was developed. Initial experiments were performed to determine whether the CRM197 observed following conventional total cell protein (TCP) isolation that was insoluble could be isolated in a soluble form. Thus, OmpA-CRM197 in the MDS42recA strain was subjected to fed-batch fermentation in defined minimal media at the 10 liter scale as described above (including incubation at 37° C. followed by a short period of incubation at 25° C. prior to the addition of inducer). The cells, containing high amounts of periplasmic CRM197, were subjected to standard detergent digestion with a commercially available non-ionic detergent-based buffer to isolate total cell protein (TCP). Samples of total cell protein were centrifuged for 10 minutes at high speed (21 k g) and the soluble fraction was isolated. Samples of TCP and the soluble fraction were analyzed. As illustrated at FIG. 9, Panel A, the soluble periplasmic form of CRM197 was rendered completely insoluble by detergent homogenization. Conversely, when periplasmic preparations (as described above) were subjected to high speed centrifugation, periplasmic CRM197 was retained in a soluble form as expected. See FIG. 9, Panel B.

In an attempt to recover the fraction of CRM197 that was insoluble, detergent-based bacterial cell lysis was compared with mechanical methods of cell lysis which would be more conducive to production-level platforms for generating CRM197 compared to detergent lysis and would eliminate the need to isolate periplasm in a commercial scale-up process. In addition, lysis was performed in the presence of chemical agents known to enhance protein solubilization as described at Table 3 below:

TABLE 3

List of lysis method and solubilization agent.

| Agent to enhance solubilization | % soluble CRM197 after sonication |
|---|---|
| Imidazole, 250 mM | 107% |
| Trehalose, 50 or 250 mM | 64%, 79% |
| Glutathione in 5:1 reduced to oxidized state | 104% |
| Glycerol, 10% | 68% |
| Sucrose, 10% | 75% |
| No agent | 88% |

Sonication and microfluidization were performed in a 50 mM TrisHCl buffer (pH 8) and all lysis methods were carried out in the presence of Lysonase™, a commercial mixture of lysozyme and benzonase (Novagen, Darmstadt, Germany). Each of the agents listed in Table 3 were then tested in separate preparations. FIG. 10 is an example of a series of isolations that were performed by detergent or mechanical lysis. Soluble CRM197 was not obtainable using detergent lysis and only small increases in soluble CRM197 were evident using detergent lysis that included solubilization agents. Glycerol and sucrose modestly enhanced the amount of soluble CRM197 found in the soluble fraction when compared to detergent alone (FIG. 10, Panel A). However, mechanical lysis dramatically increased the levels of CRM197 in the soluble fraction. In fact, a dramatic increase of CRM197 levels was evident in the soluble fraction from all samples that underwent mechanical lysis, whether sonication (FIG. 10, Panel B) or microfluidization was used. Further, the amounts of soluble CRM197 obtained following mechanical lysis did not differ markedly by solubilization agent (compare "no agent" with all other agents in Table 3). A compilation of results generated from the mechanical lysis method suggests that CRM197 in MDS42 (using culture conditions that include a short 37° C. incubation followed by growth at 25° C. and late stage induction with 25-35 μM IPTG) comprises 7.2-8.3% of the total cellular protein and between 6.3 and 7.7% of soluble protein. These results are intriguing because mechanical lysis is the standard method of cell disruption used in large scale commercial fermentations and imply the capability of generating high amounts of soluble CRM197.

Based on the aforementioned data, a suitable commercial protocol for generating soluble CRM197 comprises fermentation of reduced genome *E. coli* host carrying an expression vector encoding CRM197 coding sequence fused to a periplasmic signal sequence (e.g. encoded by ompA or ompF) at 25° C. in which the cells are collected by low speed centrifugation, lysed by mechanical means (e.g. sonication or microfluidization) in a suitable buffer (e.g. 50 mM Tris-HCl buffer at pH ~8). Following centrifugation to remove debris, soluble CRM197 is then isolated from the supernatant. In shake flask cultures incubated at 25° C. and 25-35 mM IPTG, between 95 and 100% of CRM197 was isolated in a soluble form.

A summary of the results of fermentations using reduced genome *E. coli* strain MDS69 metab (as described above) carrying an expression vector containing an ompA-CRM197 fusion is shown at Table 4 below. These fermentations occurred under fed-batch conditions using defined minimal media and the addition of inducer IPTG late in logarithmic growth. The fermentation scale was 10 liters. By altering the inducer concentration the amount of periplasmic CRM197 was increased from 0.5 to about 2 g/L.

TABLE 4

Fed-batch fermentations of strain T69 metabolic using glucose feed

| | | Max yield@ 29 hours | |
|---|---|---|---|
| Fermentation | Induction Level | OD | Soluble $CRM_{197}$ Yield |
| Ferm 157 | 25 uM | 256 | 0.74 g/L |
| Ferm 158 | 50 uM | 262 | 1.62 g/L |
| Ferm 159 | 100 uM | 291 | 1.96 g/L |

Figure 11:
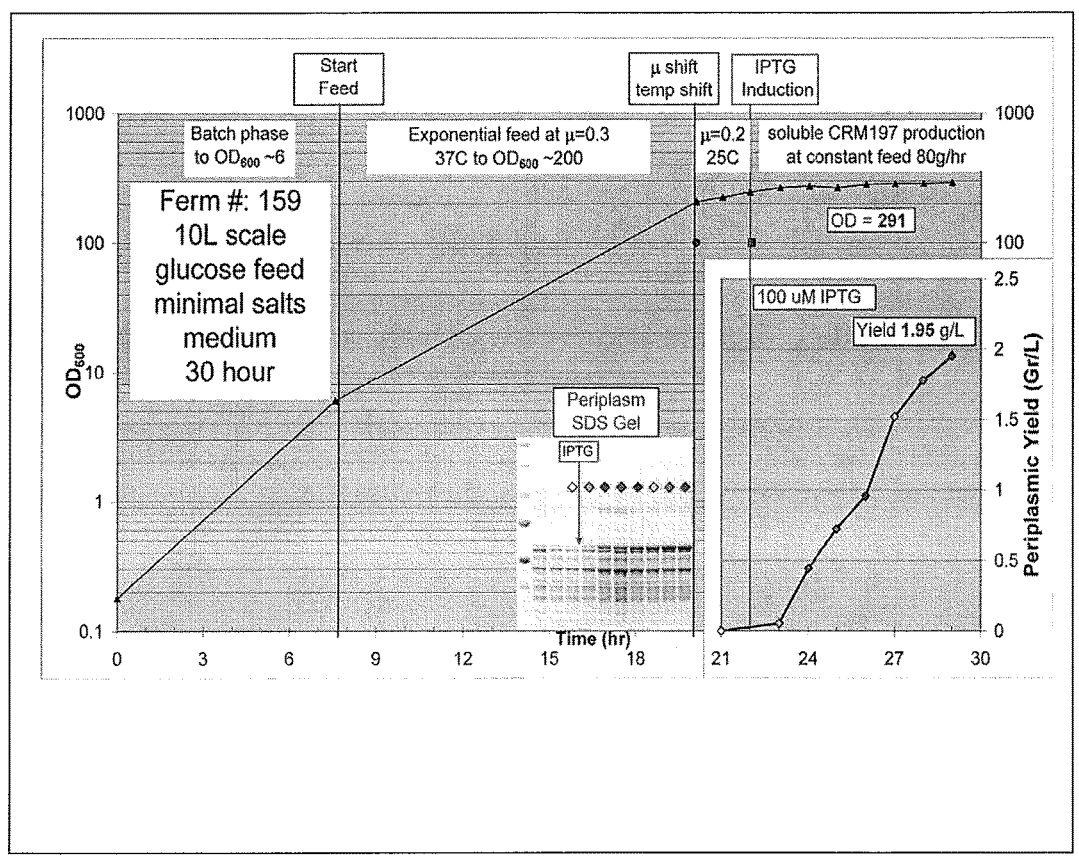
Figure 12:
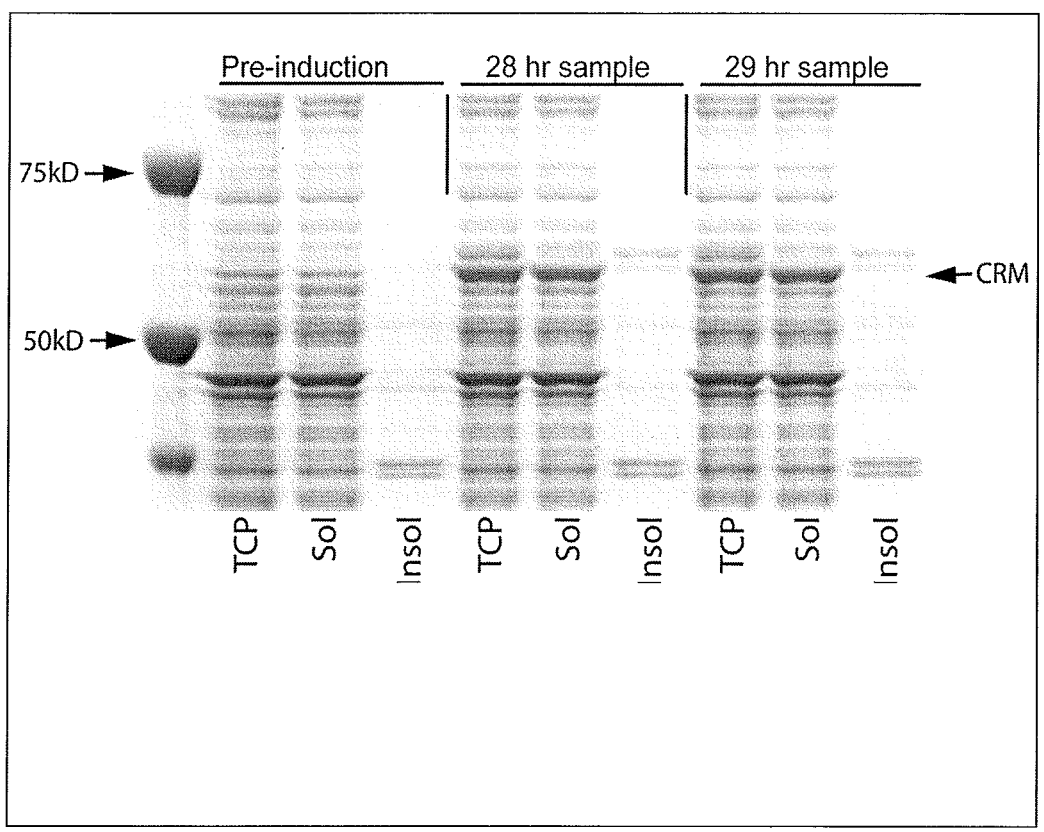

FIG. 11 illustrates specifics of the fermentation employing a 100 μM inducer concentration. Gels from this fermentation comparing total cell protein (TCP) isolates with soluble (Sol) and insoluble (Insol) fractions clearly indicated robust expression of soluble CRM197 during fermentation (see FIG. 12).

Optimal conditions for production of soluble CRM197 in fed-batch fermentation of reduced genome *E. coli* host strains were as follows. With respect to temperature, initiation of growth in the batch phase by incubating at 37° C. followed by a temperature shift to between 20 and 25° C. prior to addition of inducer (in this case IPTG) was optimal. Optimal pH range is between 6.5 and 7.5 (e.g. 6.5, 7.0 or 7.5). Optimal induction concentration is between 100 and 250 μM IPTG (added during late log phase of growth). With respect to media conditions, minimal media conditions were determined to be adequate and have the advantage of reduced cost and defined conditions free from animal derived products. Importantly, conventional *E. coli* strains do not grow robustly in minimal media. Employing these optimal conditions, it is estimated that a target yield of at least 4 g/L of soluble CRM197 can be reliably produced in 10 L scale fermentations using reduced genome *E. coli* host strains (e.g. MDS42 or MDS69).

EXAMPLE 4

Downstream Processing of CRM197

Figure 13:
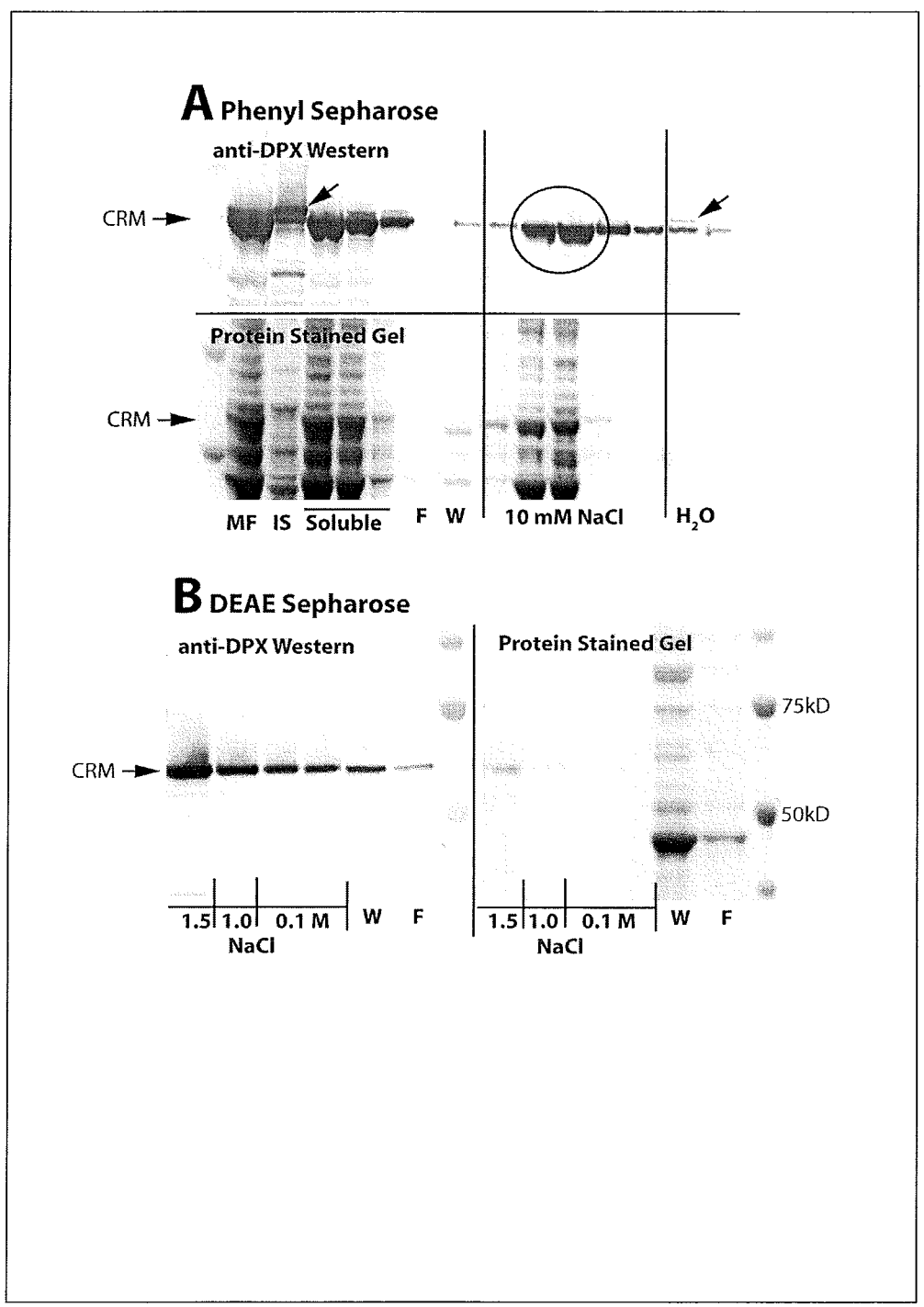

Following production of CRM197 in reduced genome *E. coli* and mechanical lysis, the CRM197 can be purified. To determine whether CRM197 produced from MDS69 metab under fermentation conditions is amenable to purification, a small scale purification was performed using a combination of hydrophobic interaction chromatography (phenyl sepharose) and anion exchange chromatography (DEAE-cellulose). 50 OD units of the 28 hr fermentation sample shown in FIG. 11 was subjected to homogenization using a microfluidizer (MF) in a 10 mM sodium phosphate buffer (pH 7.5) solution. The resulting homogenate was centrifuged at 21,000 g for 10 minutes and the soluble and insoluble (IS) fractions were isolated. Using Western blotting and polyclonal antibodies against diphtheria toxin (DPX), CRM197 was found to be highly enriched in the soluble fraction (FIG. 13, panel A compares the microfluidizer (MF) and the resuspended insoluble (IS) fraction with the pre-column soluble fraction at three concentrations (0.1, 0.07 and 0.04 OD)). The soluble fraction (25 OD equivalent) was filtered (0.45 μm), brought to 13% (wt/vol) ammonium sulfate and loaded onto a phenyl sepharose column (Phenyl sepharose HP HiTrap, General Electric) that was previously equilibrated in 10 mM sodium chloride, 10 mM sodium phosphate buffer, pH 7.5. The column was washed using 0.6 M ammonium sulfate, 6 mM sodium phosphate buffer, pH 7.5 and CRM197 was eluted under low salt conditions (10 mM sodium choloride, 10 mM sodium phosphate buffer, pH 7.5). The five 2.5 mL eluted fractions were then analyzed by anti-DPX Western blot and protein staining (FIG. 13, Panel A, lanes labeled 10 mM NaCl). A small amount of unprocessed CRM197 (FIG. 13, Panel A, arrows) was purified away from the main eluted sample with a final wash with distilled water. The fractions circled in FIG. 13 Panel A were then pooled, diluted 1:2 with distilled water and loaded onto a column containing 1 ml of DEAE sepharose fast flow (Pharmacia) that had been equilibrated in 10 mM sodium chloride, 10 mM sodium phosphate, pH 7.5. After loading the sample and collecting the flow through, the column was washed with 3 volumes of 50 mM sodium chloride, 0.5 mM sodium phosphate buffer, pH 7.5. CRM197 eluted using increasing sodium chloride concentrations: 100 mM NaCl (2 times 3 ml), 1 M NaCl (3 ml) and 1.5 M NaCl (3 ml). SDS-PAGE analysis revealed that the most highly pure soluble CRM197 was eluted using 1 M NaCl, although a significant amount still remained bound to the column.

These results indicate that CRM197 produced in reduced genome E. coli host strains is highly soluble and can be isolated to high purity using existing purification methods.

EXAMPLE 5

CRM197 Production in Reduced Genome E. coli Hosts Compared to Wild Type Strains

Periplasmic production of CRM197 in reduced genome E. coli strains was compared to the production of CRM197 in wild type E. coli strains under similar conditions. Thus, CRM197 E. coli BLR(DE3) strain was transformed with pSX2 vector carrying an OmpA-CRM197 fusion and periplasmic production was assessed and compared to periplasmic production of CRM197 in reduced genome E. coli strain MDS42recA. Fermentation conditions were as described above. Following a brief growth initiation phase at 37° C., cells were grown in Korz media supplemented with 0.2% glucose (and 31 µg/ml of Isoleucine for BLR(DE3) cultures) at 25° C. for 19 hours. Expression of CRM197 was induced at OD=0.3 with 15 or 25 mM IPTG.

Figure 14:
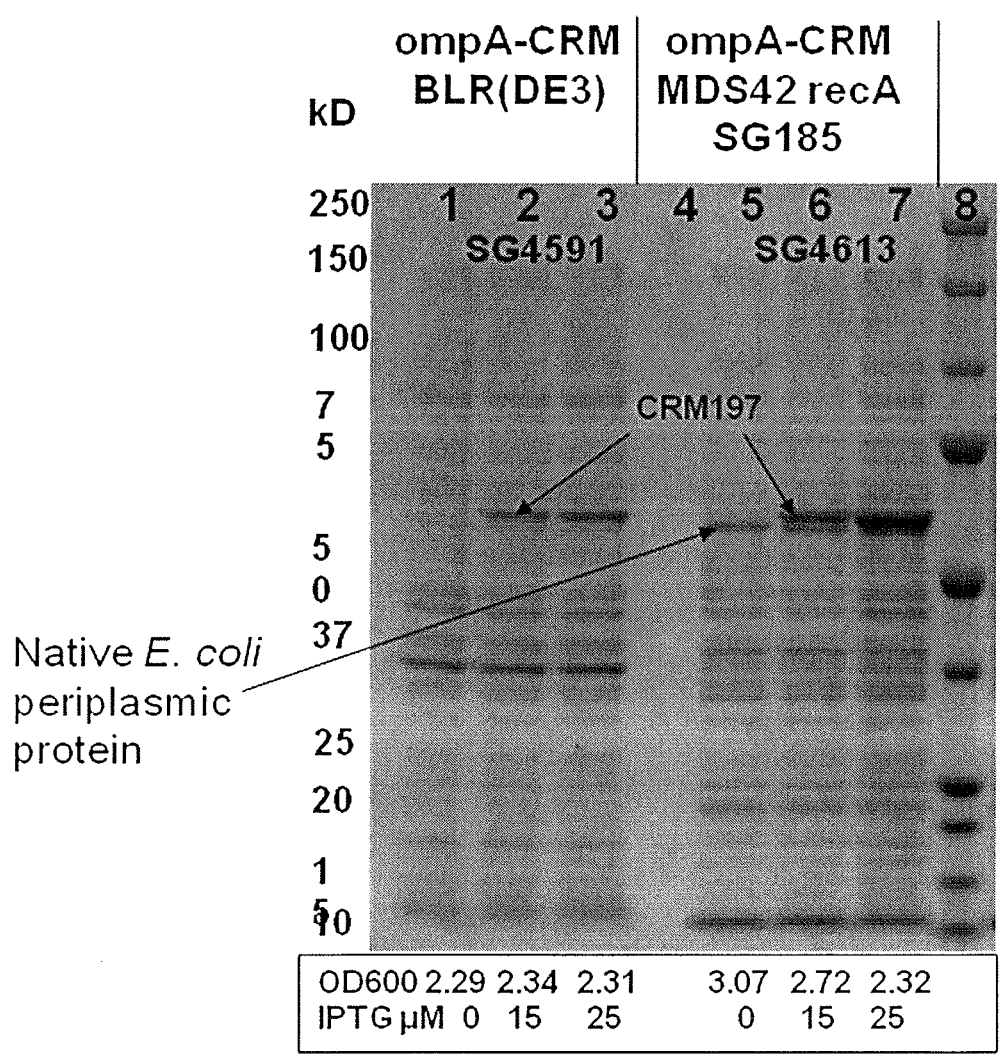

As illustrated at FIG. 14, at least a ~5-fold increase in production of periplasmic CRM197 was observed in the reduced genome E. coli host compared to the wild type B strain.

Figure 15:
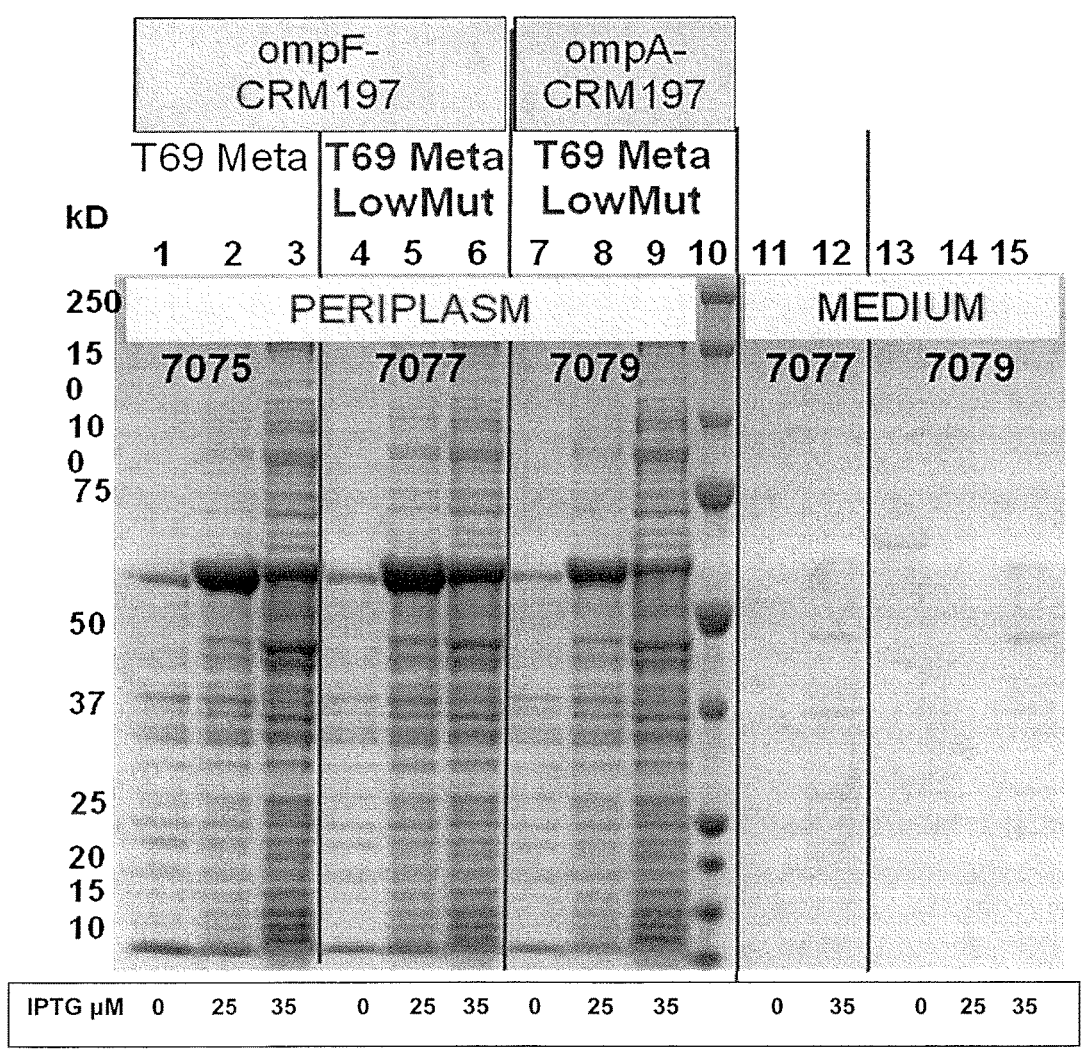

Additional experimentation revealed that the OmpF-CRM197 fusion actually resulted in a higher amount of soluble periplasmic CRM197 in reduced genome E. coli hosts compared to the OmpA-CRM197 fusion. Reduced genome E. coli host strain MDS69 metab and MDS69 lowmut (MDS69 strain further comprising deletions of polB (b0060), dinB (b0231) and umuDC (b1183-b1184)) were transformed with an expression vector encoding an OmpF-CRM197 fusion and periplasmic expression of CRM197 was compared to that in a MDS69 lowmut host carrying an expression vector encoding an OmpA-CRM197 fusion under the same conditions. Following a brief growth initiation phase at 37° C., cells were grown in Korz media supplemented with 0.2% glucose at 25° C. for 23 hours. Expression of CRM197 was induced at OD=0.3 to 0.34 with 25 or 35 mM IPTG. Periplasmic proteins were isolated and the expression of soluble CRM197 in each strain was analyzed. As illustrated at FIG. 15, a higher yield of CRM197 was obtained with the OmpF-CRM197 construct compared to the OmpA-CRM197 construct.

EXAMPLE 6

Testing CRM197 Production with a Variety of Signal Sequences in a Reduced Genome E. coli Strain Signal sequences were selected based on their abundance in the periplasm of E. coli B and K strains as determined by 2D gel analysis of periplasmic fractions (Han, Mee-Jung et al., Journal of Bioscience and Bioengineering, 117(4):437-442 (2014)). Table 5 lists the signal sequences selected and their relative abundance in the periplasm of B and K strains:

TABLE 5

| Protein | Abundance in Periplasmic Fraction (B and/or K) | Gene/Protein Function |
| --- | --- | --- |
| MglB | K | methyl galactose transporter |
| MalE | B + K | maltose transporter |
| OppA | B + _K | oligopeptide transporter |
| RbsB | B + K | subunit ribose transporter |
| Agp | B > K | glucose-1 phosphatase, 3-phytase |
| FkpA | B > K | peptidyl-prolyl cis-trans isomerase; in protein folding |
| YtfQ | B >> K | galactofuranose binding protein, subunit ABC transporter |
| HdeA | K | Stress response induced by acidic conditions |
| HdeB | K | Stress response induced by acidic conditions |
| GlnH | B > K | subunit of glutamine ABC transporter |

Figure 17:
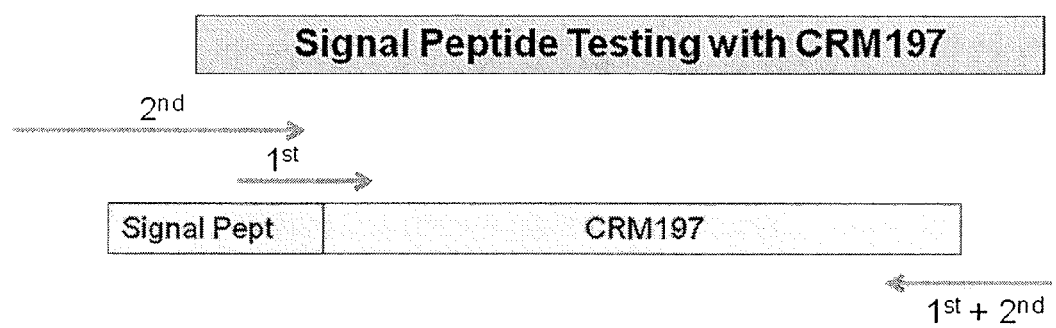

Plasmid pSX2 containing the combinations of signal sequence and CRM197 sequence (lacking its native signal sequence) illustrated at Table 5 and FIG. 17 (MglB, MalE, OppA, RbsB, Agp, FkpA, YtfQ, HdeA, HdeB or GlnH; OmpF and OmpC were tested as well) was transformed into reduced genome E. coli strain MDS69 metab (T69 Meta in FIGS. 18-21) and examined in shake flask culture. As described above, MDS69 metab comprises the following modifications on an MDS69 background (i) deletion of the iclR (b-number b4018, described at NCBI Entrez GeneID No. 948524) and arpA genes (b-number b4017, described at NCBI Entrez GeneID No. 944933) (ii) deletion of the rph gene (b3643), and (iii) correction of the ilvG frameshift mutation by insertion of an AT dinucleotide at position 982. Briefly, colony forming units of the transformed bacteria from MOPS minimal medium-kanamycin (MMM/Kan)-glucose streak plates were resuspended in 3 ml Korz minimal medium supplemented with 0.2% glucose and 50 µg/ml Kanamycin and incubated at 37° C. overnight to generate the starter culture. Starter culture was used to inoculate 20 ml Korz/0.2% glucose/Kan in 125 ml Erlenmeyer-flasks to OD600=0.05 and grown at 37° C. for 1.5 hours and then shifted to 25° C. and grown until $OD_{600}$ ~0.3. At that point, inducer (IPTG) was added at 25 µM, 35 µM or 50 concentration (late induction). The late inductions were then grown at 25° C. for 20 hours and 2 ODs of culture were harvested. Total cell protein was prepared using BugBuster+Lysonase and periplasmic and spheroplast fractions were prepared using Epicentre Periplasting Method.

Figure 18:
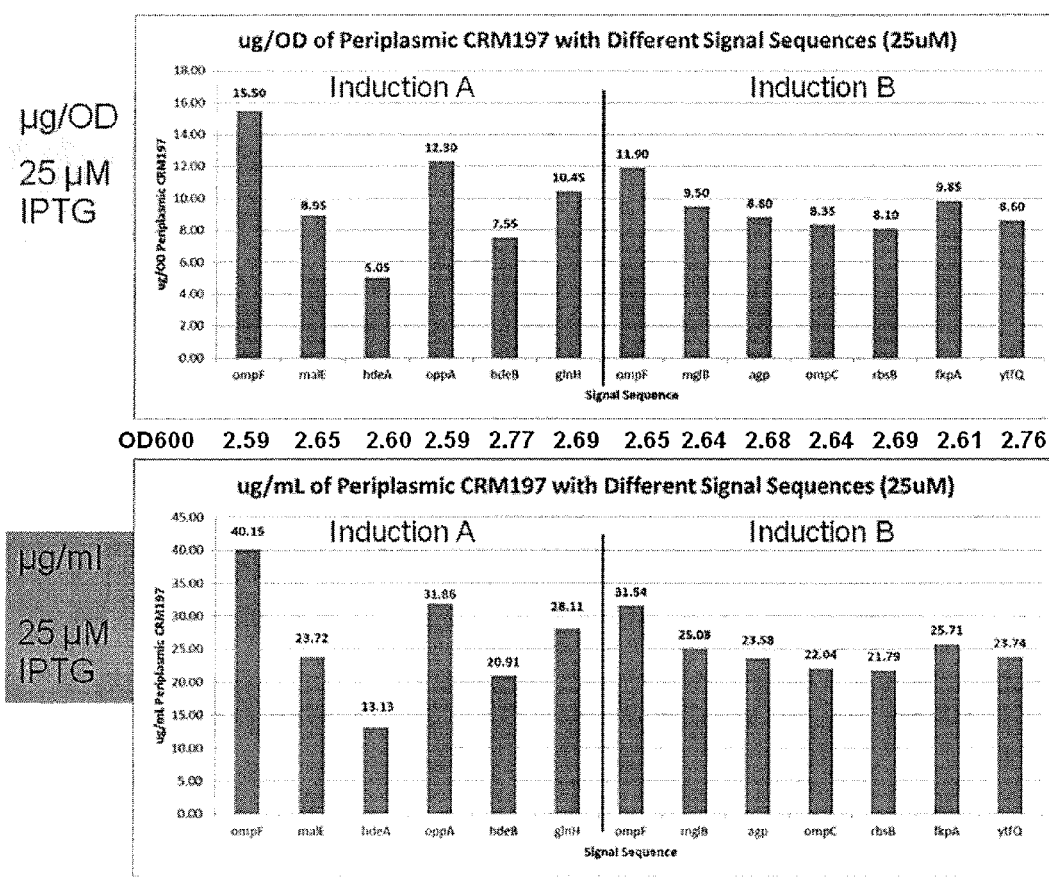
Figure 19:
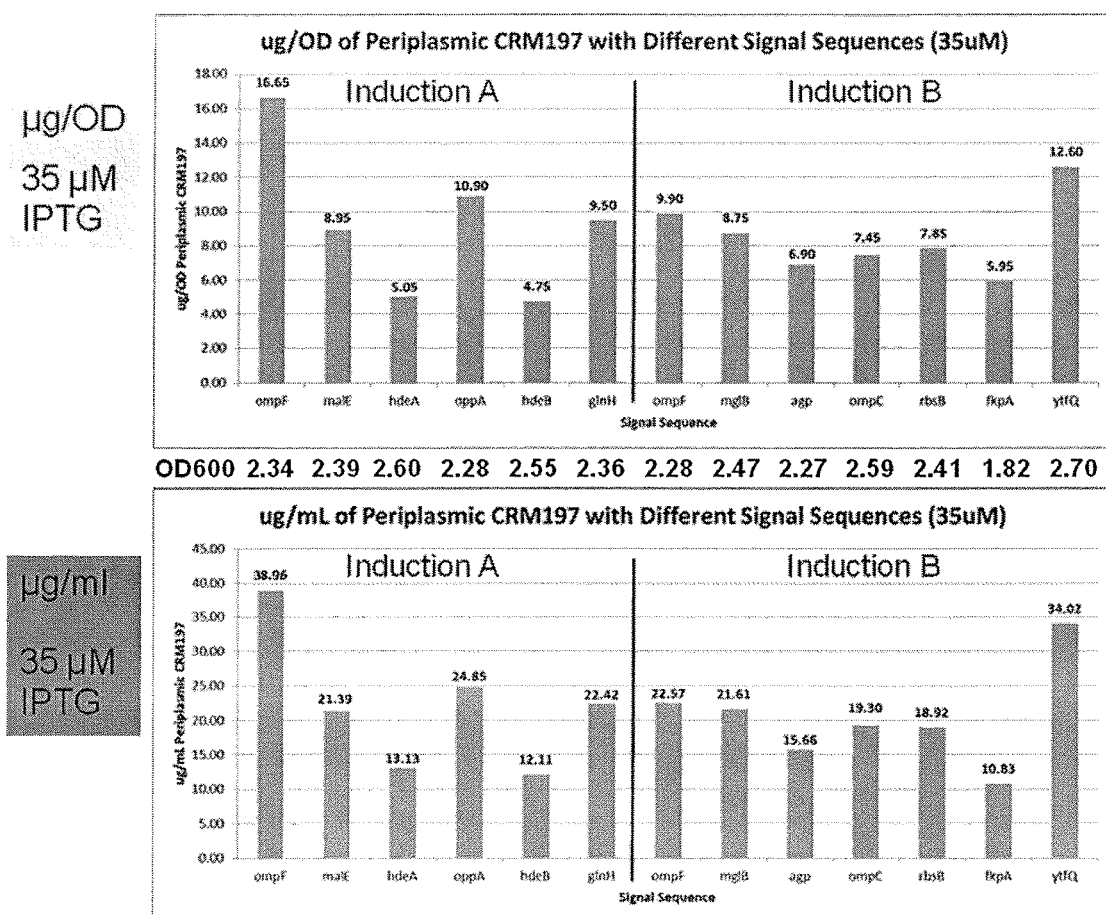
Figure 20:
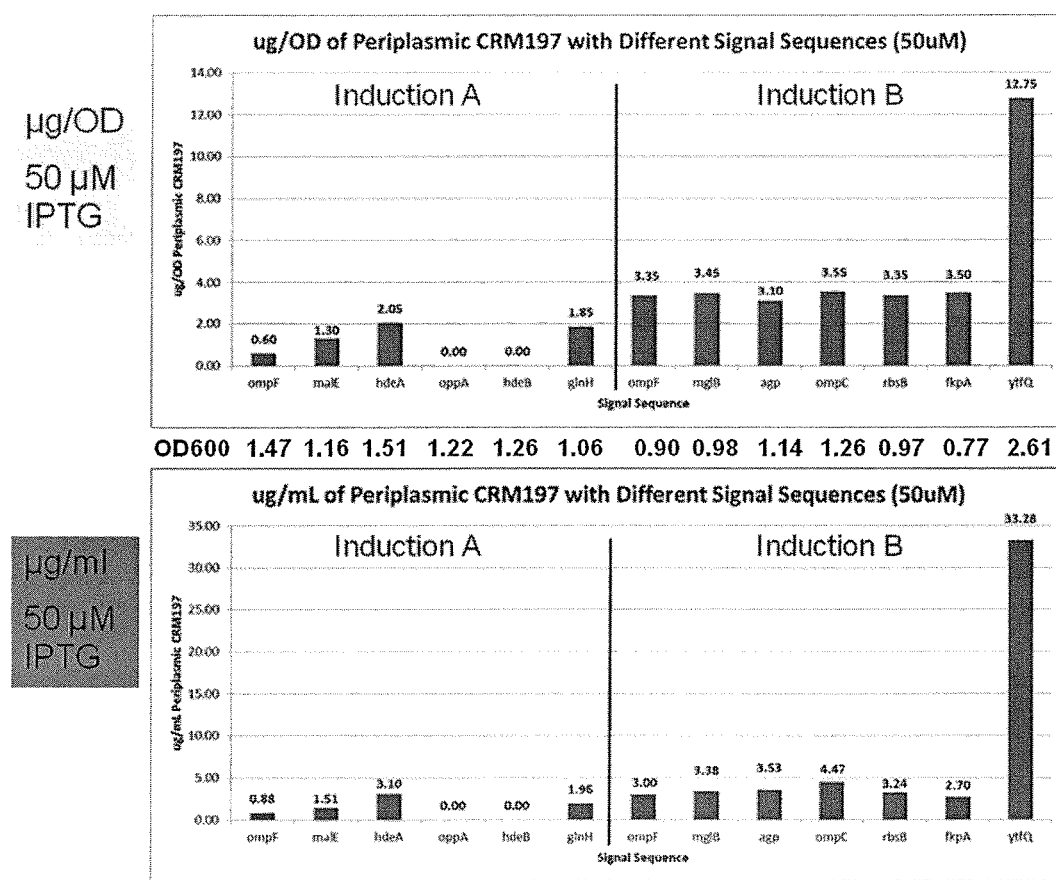

FIGS. 18-20 depict the periplasmic yield of (soluble) CRM197 at 25 µM, 35 µM or 50 µM inducer concentration respectively using the indicated signal sequences (Induction A—OmpF, MalE, HdeA, OppA, HdeB, GlnH; Induction B—OmpF, MglB, Agp, OmpC, RbsB, FkpA, YtfQ). Good yield was obtained with all signal sequences at the 25 µM inducer concentrations (FIG. 18). Interestingly, at the 35 µM inducer concentration, yield of CRM197 with the YtfQ signal sequence significantly increased relative to the yield of CRM197 obtained at this inducer concentration with the other tested signal sequences (FIG. 19). This effect became even more significant at the 50 μM inducer concentration, with the yield of CRM197 remaining high whereas the yield of CRM197 with the other tested signal sequences was significantly reduced at this inducer concentration (FIG. 20). Thus, the combination of CRM197 and YtfQ signal sequence was determined to have a significantly broader induction range than the combination of CRM197 with the other signal sequences tested.

To further assess the induction range for CRM197 with the YtfQ signal sequence, two cultures each of 8 IPTG (inducer) levels were tested in MDS69 metab (0, 25, 35, 50, 75, 100, 150 and 250 μM) according to the method described above. As a control, 2 cultures each of 4 IPTG levels for MDS69 metab with CRM197 and the OmpF signal sequence were also tested (0, 25, 35, 50 μM). 2 OD samples were collected for total cell protein (TCP) and periplasmic analysis on Caliper.

Figure 21:
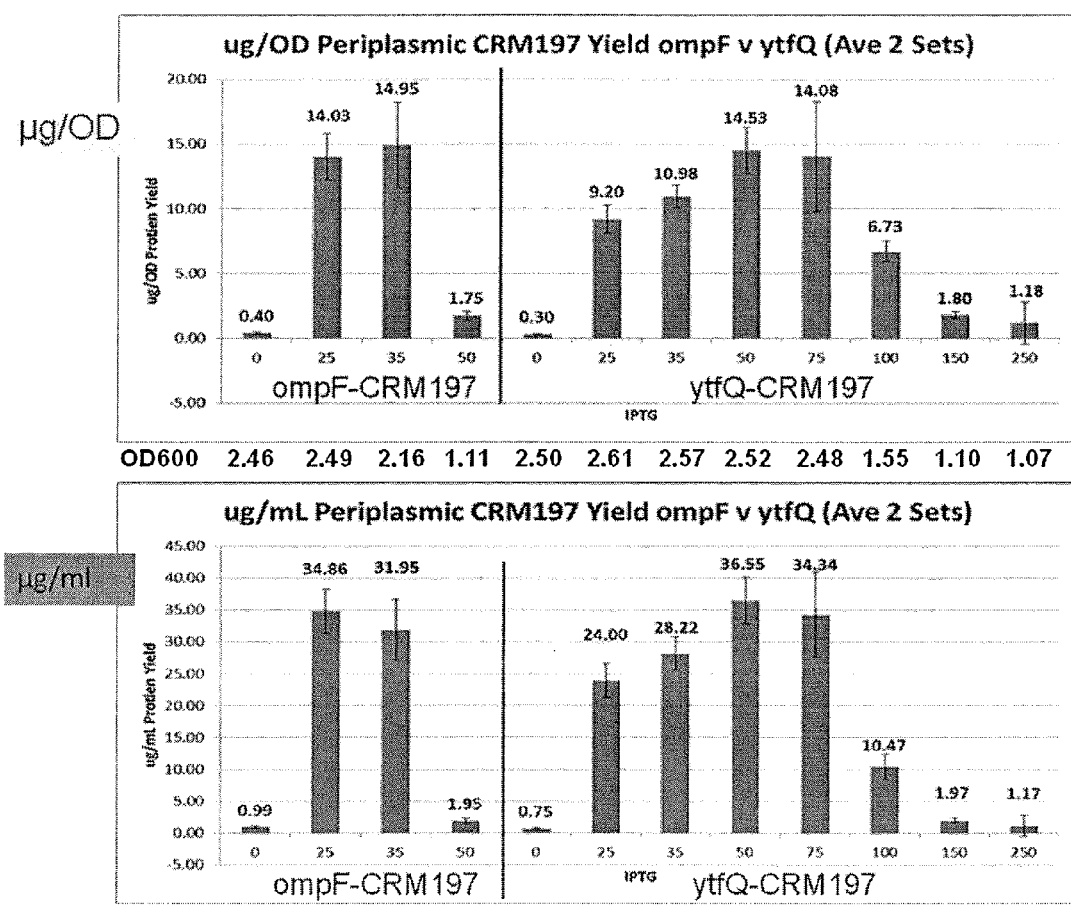
Figure 22:
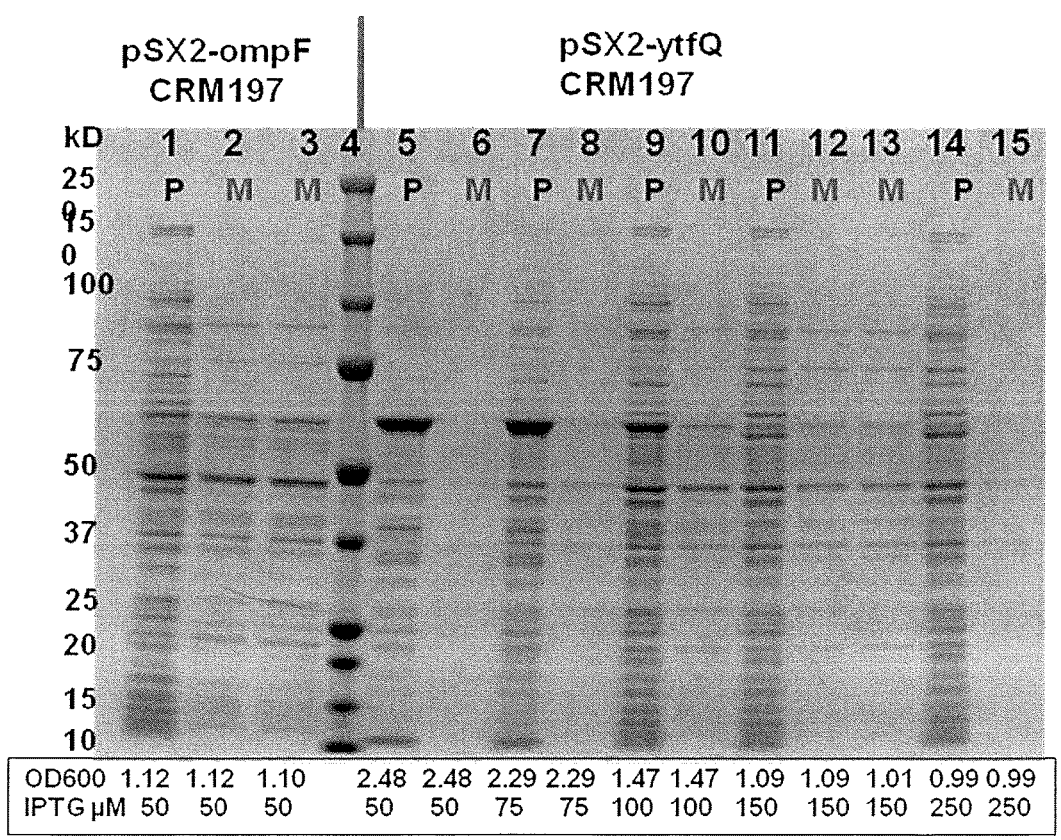

The averaged results of the two cultures tested for each inducer level is illustrated at FIG. 21. Yield of CRM197 in combination with the YtfQ signal sequence (YtfQ-CRM197) remained high across all inducer levels up to 100 μM. Yield of CRM197 in combination with OmpF, however, was high only at the 25 and 35 μM inducer concentrations. FIG. 22 is a protein gel comparing the effect of OmpF and YtfQ signal sequence on CRM197 yield in periplasm (P) and media (M) at 50 μM IPTG (OmpF) and at 50, 75, 100, 150 and 250 μM IPTG (YtfQ). A surprisingly large amount of periplasmic CRM197 was evident at the 50, 75 and 100 μM inducer concentration for the YtfQ signal sequence whereas a much smaller amount of periplasmic CRM197 was present at the 50 μM inducer concentration for the OmpF sequence.

"Briefly, colony forming units of the transformed bacteria from MOPS minimal medium-kanamycin (MMM/Kan)-glucose streak plates were resuspended in 3 ml Korz minimal medium supplemented with 0.2% glucose and 50 μg/ml Kanamycin and incubated at 37° C. overnight to generate the starter culture. Starter culture was used to inoculate 20 ml Korz/0.2% glucose/Kan in 125 ml Erlenmeyer-flasks with $OD_{600}$=0.05 and grown at 37° C. for 1.5 hours and then shifted to 25° C. until $OD_{600}$ ~0.3. At that point, inducer (IPTG) was added at 25 μM, 35 μM or 50 μM concentration (late induction). The late inductions were then grown at 25° C. for 20 hours and 2 ODs of culture were harvested. Total cell protein was prepared using BugBuster+Lysonase and periplasmic and spheroplast fractions were prepared using Epicentre Periplasting Method"

Figure 23:
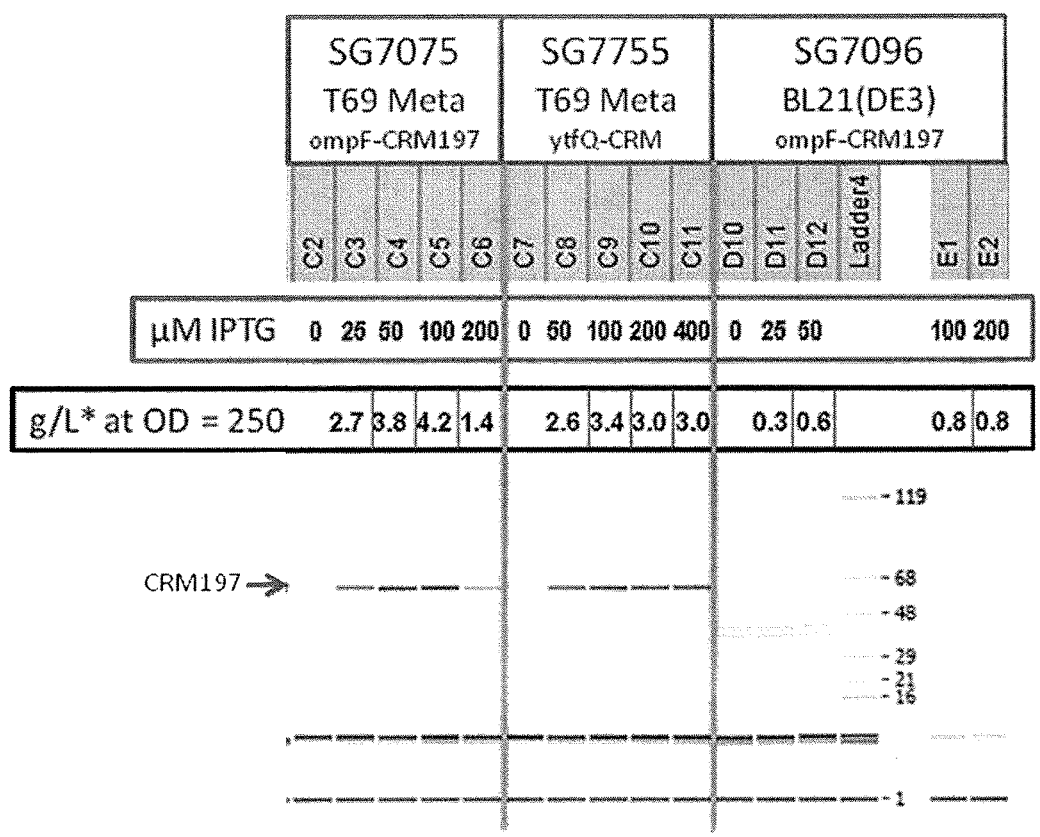

Next, the effect of very late induction ($OD_{600}$~2) on CRM197 yield in combination with either OmpF or YtfQ signal sequence in MDS69 metab and in combination with OmpF in an *E. coli* B strain (BL21DE3) was assessed. Briefly, 3 ml Korz minimal medium supplemented with 0.2% glucose and 50 μg/ml Kanamycinin was inoculated with colony forming units of transformed MDS69 metab or BL21DE3, incubated at 37° C. overnight and used to inoculate 15 ml of Korz minimal medium supplemented with 0.2% glucose and 50 μg/ml Kanamycinin in 125 ml Erlenmeyer Flasks which was grown overnight at 25° C. to generate the 25° C. starter culture. The starter culture was used to inoculate 90 ml Korz/0.2% glucose/kanamycin in 500 ml Erlenmeyer flasks to $OD_{600}$=0.1 followed by growth at 25° C. until the $OD_{600}$>2 (saturated or near saturated) and then split into 4×20 aliquots in 125 ml Erlenmeyer flasks for induction at various IPTG concentrations (very late induction). The inductions were grown at 25° C. for 20 hours, and 2 ODs of culture harvested for analysis. Total cell protein (TCP) was prepared using BugBuster+Lysonase. Periplasmic and spheroplast fractions were prepared using the Epicentre Periplasting Method. As shown in FIG. 23, good periplasmic expression up to 100 μM IPTG was observed for the combination of CRM197 and OmpF signal sequence in MDS69 metab which decreased at 200 mM inducer concentration, presumably due to insolubility. Good periplasmic expression was observed for the combination of CRM197 and YtfQ signal sequence in MDS69 metab up to 400 μM IPTG (the highest concentration tested) with no insoluble CRM197 observed. Weak expression was observed for the combination of CRM197 and OmpF in BL21(DE3) strain at all inducer concentrations tested (25-200 μM). CRM197 was not observed in spheroplasts.

Summary—The data presented demonstrates that production of soluble CRM197 in reduced genome *E. coli* hosts delivered yields that were 10 times that obtained by conventional methods. Production in the reduced genome *E. coli* hosts is expected to increase the efficiency and reduce manufacturing costs. Moreover, production in reduced genome *E. coli* hosts will also be cleaner and safer than that produced in conventional bacteria with non-reduced genomes. These improvements will have a wide impact on production of pharmaceutical protein products and ultimately broaden access to vaccines for at-risk populations who need them. Moreover, high yield of CRM197 was observed in combination with a broad range of signal sequences. The broad induction range observed for YtfQ signal sequence in combination with CRM197 was surprising since YtfQ is found in much larger quantities in B strain *E. coli* compared to K strain *E. coli* and the exemplified reduced genome strains are based on a K strain. The broad induction range of CRM197 in combination with YtfQ in reduced genome *E. coli* is a significant advantage because the concentration of inducer can vary during production of the protein and accordingly the use of the YtfQ signal sequence in combination with CRM197 in these hosts results in a further increase in yield of CRM197.

What is claimed is:

1. A method for producing a recombinant CRM197 in a reduced genome E. coli host, the method comprising incubating a reduced genome E. coli comprising an expression vector comprising a nucleotide sequence encoding a CRM197 protein fused to an ompA, ompF or ytfQ signal sequence that directs transfer of the CRM197 protein to the periplasm, said nucleotide sequence operably linked to an expression control sequence, under conditions suitable for the expression of the recombinant CRM197 protein, whereby a yield of at least 1 gram per liter of soluble CRM197 is obtained, wherein the native parent strain of the reduced genome E. coli host is an E. coli K-12 strain comprising a native −2 frameshift mutation in the ilvG gene, and wherein the reduced genome E. coli host comprises the following modifications relative to the native parent E. coli strain: (i) deletion of at least the following DNA segments: b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153 and b2945 of the E. coli K12 strain MG1655 or the corresponding DNA segments in another E. coli K12 strain (ii) deletion of the rph gene to enhance orotate phosphoribosyltransferase activity (iii) correction of the native −2 frameshift mutation in the ilvG gene in order to restore the active acetohydroxy acid synthase II production and (iv) deletion of all or part of the iclR and arpA genes.

2. The method of claim 1, whereby a yield of at least 2 grams per liter of soluble CRM197 is obtained.

3. The method of claim 1, wherein the signal sequence is OmpF or YtfQ.

4. The method of claim 3, wherein the signal sequence is YtfQ.

5. The method of claim 1, wherein the reduced genome E. coli has additionally deleted therefrom at least the following DNA segments: b0315-b0331, b0333-b0341, b0346-b0354, b2481-b2492, b2219-b2230, b4500, b3707-b3723, b0644-b0650, b4079-4090, b4487, b4092-b4106, b0730-b0732, b3572-b3587, b1653, b2735-b2740, b2405-b2407, b3896-b3900, b1202, b4263-b4268, b0611, b2364-b2366, b0839, b0488-b0500, and b0502 of the E. coli K-12 strain MG1655 or the corresponding DNA segments in another E. coli K-12 strain.

6. The method of claim 1, wherein the reduced genome E. coli comprises a functional recA (b2699) gene.

7. The method of claim 1, wherein the reduced genome E. coli comprises a relA gene having at least one point mutation at position 547 or 548 of the coding sequence of the relA gene, wherein the mutation is selected from one or more of: a G→A mutation at position 547, a G→T mutation at position 547, a C→G mutation at position 548, or a C→T mutation at position 548.

8. The method of claim 1, wherein the CRM197 nucleotide sequence is optimized for expression in the E. coli host cell.

9. The method of claim 1 comprising
(a) growing the reduced genome E. coli and
(b) inducing expression of CRM197.

10. The method of claim 9, wherein the method is carried out in a fermentor.

11. The method of claim 9, wherein step (a) comprises growing the reduced genome E. coli at 37° C. for up to 19 hours followed by growth at about 20-30° C. prior to and subsequent to step (b).

12. The method of claim 9, wherein steps (a) and (b) are performed in growth medium that does not comprise serum, yeast extract or other animal by-products.

13. The method of claim 10, wherein in step (a) the pH ranges between 6.5 and 7.5.

14. The method of claim 13, wherein the pH is maintained using a phosphate buffer, a Tris buffer or a histidine buffer.

15. The method of claim 14, wherein the buffer is a phosphate buffer.

16. The method of claim 9, wherein expression is induced in step (b) by addition of a suitable amount of IPTG.

17. The method of claim 10, wherein expression is induced at an $OD_{600}$ of from 100 to 400.

18. The method of claim 10 wherein the fermentor contains 0.5-50,000 liters of culture.

19. The method of claim 9 comprising a further step of (c) mechanically disrupting the cultured reduced genome E. coli cells in the absence of detergent and centrifuging the resulting cell lysate to obtain a soluble fraction.

20. The method of claim 19, wherein the mechanical disruption comprises sonication or microfluidization.

21. The method of claim 19, wherein CRM197 is purified from the soluble fraction by one or more purification steps.

22. The method of claim 21, wherein the one or more purification steps comprises hydrophobic interaction chromatography and/or anion exchange chromatography.

23. The method of claim 22, wherein the purification steps comprise hydrophobic interaction chromatography followed by anion exchange chromatography.

24. The method of claim 1, wherein the native parent *E. coli* strain is K-12 strain MG1655.

25. The method of claim 1, wherein the reduced genome *E. coli* lacks a functional recA (b2699) gene.

26. The method of claim 1, wherein the reduced genome *E. coli* does not comprise insertion sequences.

27. The method of claim 1, wherein the reduced genome *E. coli* lacks a functional dinB (b0231) gene and optionally lacks functional polB (b0060) and/or umuDC (b1183-b1184) genes.

28. A reduced genome *E. coli* host comprising an expression vector comprising a nucleotide sequence encoding a CRM197 protein fused to an ompA, ompF or ytfQ signal sequence that directs transfer of the CRM197 protein to the periplasm, wherein said nucleotide sequence is operably linked to an expression control sequence, wherein the native parent E. coli strain of the reduced genome *E. coli* host is a K-12 strain comprising a native--2 frameshift mutation in the ilvG gene, and wherein the reduced genome E. coli host comprises the following modifications relative to the native parent *E. coli* strain: (i) deletion of at least the following DNA segments: b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-4468, b1137-b1172, b0537-b0565, b0016-b0022, b4412-b4413, b0577-b0582, b4415, b2389-b2390, b2392-b2395, b0358b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153 and b2945 of the *E. coli* K12 strain MG1655 or the corresponding DNA segments in another *E. coli* K12 strain (ii) deletion of the rph gene to enhance orotate phosphoribosyltransferase activity (iii) correction of the native −2 frameshift mutation in the ilvG gene in order to restore the active acetohydroxy acid synthase II production and (iv) deletion of all or part of the iclR and arpA genes.

29. The reduced genome *E. coli* host according to claim 28, wherein the native parent *E. coli* strain is K-12 strain MG1655.

30. A method for producing a recombinant CRM197 in a reduced genome *E. coli* host comprising incubating a reduced genome *E. coli* comprising an expression vector comprising a nucleotide sequence encoding a CRM197 protein fused to an ompA, ompF or ytfQ signal sequence that directs transfer of the CRM197 protein to the periplasm, said nucleotide sequence operably linked to an expression control sequence, under conditions suitable for the expression of the recombinant CRM197 protein, whereby a yield of at least 1 gram per liter of soluble CRM197 is obtained, wherein the native parent *E. coli* strain of the reduced genome *E. coli* host is a K-12 strain and wherein the reduced genome *E. coli* host comprises a deletion of at least the following DNA segments relative to the native parent *E. coli* strain: b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-4468, b1137-b1172, b0537-b0565, b0016-b0022, b4412-b4413, b0577-b0582, b4415, b2389-b2390, b2392-b2395, b0358b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153 and b2945 of the *E. coli* K-12 strain MG1655 or the corresponding DNA segments in another *E. coli* K-12 strain.

31. The method of claim 30, wherein the reduced genome *E. coli* host is strain MDS42.

32. The method of claim 30, wherein the reduced genome *E. coli* has additionally deleted therefrom at least the following DNA segments: b0315-b0331, b0333-b0341, b0346-b0354, b2481-b2492, b2219-b2230, b4500, b3707-b3723, b0644-b0650, b4079-4090, b4487, b4092-b4106, b0730-b0732, b3572-b3587, b1653, b2735-b2740, b2405-b2407, b3896-b3900, b1202, b4263-b4268, b0611, b2364-b2366, b0839, b0488-b0500, and b0502 of the E. coli K-12 strain MG1655 or the corresponding DNA segments in another *E. coli* K-12 strain.

33. The method according to claim 10, wherein the method comprises fed-batch fermentation.

* * * * *

SEQUENCE LISTING

```
<160> NUMBER OF SEQ ID NOS: 38

<210> SEQ ID NO 1
<211> LENGTH: 1608
<212> TYPE: DNA
<213> ORGANISM: Artificial Sequence
<220> FEATURE:
<223> OTHER INFORMATION: CRM197 sequence optimized for periplasmic
      expression
```

<400> SEQUENCE: 1

```
ggtgcggatg atgttgtgga cagctctaag tcttttgtga tggaaaactt tagctcgtac     60
cacggtacga agccaggtta tgtcgacagc attcaaaaag gtatccagaa accgaagtcc    120
ggcacgcagg gtaactacga cgacgattgg aaagagttct acagcaccga caacaagtat    180
gacgcagcgg gttacagcgt tgacaatgag aatccgttga gcggcaaagc gggtggtgtt    240
gtcaaagtga cgtatccggg tctgaccaag gtcctggcgt tgaaagttga taacgcggaa    300
accattaaga aagagctggg tctgagcctg accgagccgt tgatggagca agttggtacc    360
gaagagttta tcaaacgttt cggcgatggt gcgagccgcg ttgtcctgtc cctgcctttc    420
gcggagggca gctccagcgt tgagtatatc aataactggg agcaagcaaa agcgctgtcc    480
gtcgaactgg aaatcaattt tgaaacgcgc ggtaaacgtg tcaagatgc aatgtacgag    540
tatatggccc aggcctgcgc tggtaatcgt gttcgtcgca gcgttggtag cagcttgtct    600
tgtatcaacc tggattggga tgtgatccgt gataagacca agactaagat cgagagcctg    660
aaagaacatg gcccgattaa gaacaagatg tcggagagcc cgaataagac cgtgagcgaa    720
gaaaaggcca agcagtatct ggaagagttc accaaacgg ctctggagca tccggagctg    780
agcgagctga aaacggttac gggcaccaac ccggtgttcg caggtgcgaa ttacgcggcg    840
tgggcagtga atgtggcgca ggtcatcgac tccgaaacgg cggacaattt ggagaaaacc    900
accgcagcgc tgagcattct gccgggcatc ggcagcgtta tgggcattgc agatggtgct    960
gtgcaccata acactgaaga aatcgtagcg caaagcattg ccctgtctag cttgatggtg   1020
gcgcaggcta ttccgctggt cggcgaactg gttgatatcg gctttgctgc ctacaacttc   1080
gttgaaagca tcattaacct gtttcaggtg gtccacaaca gctataatcg cccagcgtac   1140
agcccgggtc acaagaccca accgttcctg cacgatggct atgcggtgtc ttggaacacg   1200
gtcgaagata gcatcattcg taccggtttc cagggcgaga gcggccatga catcaagatt   1260
actgcagaaa atacccccgct gccgatcgca ggtgtcctgc tgcctacgat tccgggtaag   1320
ctggacgtta acaaaagcaa aacccacatt tctgtgaacg gtcgtaagat tcgcatgcgt   1380
tgtcgtgcga ttgacggcga cgtcaccttc tgccgtccga agagcccggt ctacgttggt   1440
aatggtgtgc acgcgaacct gcacgtggcg tttcaccgca gcagctcgga gaaaatccat   1500
agcaatgaga tttctagcga cagcattggc gttctgggtt accaaaagac ggttgaccat   1560
accaaagtca attccaaact gagcctgttc tttgagatca aaagctaa                1608
```

<210> SEQ ID NO 2
<211> LENGTH: 535
<212> TYPE: PRT
<213> ORGANISM: Artificial Sequence
<220> FEATURE:
<223> OTHER INFORMATION: Expressed and processed CRM197 amino acid
      sequence

<400> SEQUENCE: 2

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60
```

```
Tyr Ser Val Asp Asn Glu Asn Pro Leu Ser Gly Lys Ala Gly Gly Val
 65                  70                  75                  80

Val Lys Val Thr Tyr Pro Gly Leu Thr Lys Val Leu Ala Leu Lys Val
                 85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
```

```
            485                 490                 495
Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
            515                 520                 525

Leu Phe Phe Glu Ile Lys Ser
            530                 535

<210> SEQ ID NO 3
<211> LENGTH: 1611
<212> TYPE: DNA
<213> ORGANISM: Artificial Sequence
<220> FEATURE:
<223> OTHER INFORMATION: CRM197 sequence optimized for expression in
      cytoplasm

<400> SEQUENCE: 3
atgggcgcag atgacgtagt agacagcagc aaaagcttcg tgatggaaaa ctttagctcg      60
taccacggta cgaagccagg ttatgtcgac agcattcaaa aaggtatcca gaaaccgaag     120
tccggcacgc agggtaacta cgacgacgat tggaagagt tctacagcac cgacaacaag     180
tatgacgcag cgggttacag cgttgacaat gagaatccgt tgagcggcaa agcgggtggt     240
gttgtcaaag tgacgtatcc gggtctgacc aaggtcctgg cgttgaaagt tgataacgcg     300
gaaaccatta gaaagagct gggtctgagc ctgaccgagc cgttgatgga gcaagttggt     360
accgaagagt ttatcaaacg tttcggcgat ggtgcgagcc gcgttgtcct gtccctgcct     420
ttcgcggagg gcagctccag cgttgagtat atcaataact gggagcaagc aaaagcgctg     480
tccgtcgaac tggaaatcaa ttttgaaacg cgcggtaaac gtggtcaaga tgcaatgtac     540
gagtatatgg cccaggcctg cgctggtaat cgtgttcgtc gcagcgttgg tagcagcttg     600
tcttgtatca acctggattg ggatgtgatc cgtgataaga ccaagactaa gatcgagagc     660
ctgaaagaac atgccccgat taagaacaag atgtcggaga cccgaataa gaccgtgagc     720 gaagaaaagg ccaagcagta tctggaagag ttccaccaaa cggctctgga gcatccggag     780
ctgagcgagc tgaaaacggt tacgggcacc aacccggtgt tcgcaggtgc gaattacgcg     840
gcgtgggcag tgaatgtggc gcaggtcatc gactccgaaa cggcggacaa tttggagaaa     900
accaccgcag cgctgagcat tctgccgggc atcggcagcg ttatgggcat tgcagatggt     960
gctgtgcacc ataacactga agaaatcgta gcgcaaagca ttgccctgtc tagcttgatg    1020
gtggcgcagg ctattccgct ggtcggcgaa ctggttgata tcggctttgc tgcctacaac    1080
ttcgttgaaa gcatcattaa cctgtttcag gtggtccaca acagctataa tcgcccagcg    1140
tacagcccgg gtcacaagac ccaaccgttc ctgcacgatg ctatgcggt gtcttggaac    1200 acggtcgaag atagcatcat tcgtaccggt ttccagggcg agagcggcca tgacatcaag    1260
attactgcag aaaatacccc gctgccgatc gcaggtgtcc tgctgcctac gattccgggt    1320
aagctggacg ttaacaaaag caaaacccac atttctgtga cggtcgtaa gattcgcatg    1380 cgttgtcgtg cgattgacgg cgacgtcacc ttctgccgtc gaagagccc ggtctacgtt    1440 ggtaatggtg tgcacgcgaa cctgcacgtg gcgtttcacc gcagcagctc ggagaaaatc    1500
catagcaatg agatttctag cgacagcatt ggcgttctgg gttaccaaaa gacggttgac    1560
cataccaaag tcaattccaa actgagcctg ttctttgaga tcaaaagcta a            1611

<210> SEQ ID NO 4
<211> LENGTH: 22
```

<212> TYPE: PRT
<213> ORGANISM: Artificial Sequence
<220> FEATURE:
<223> OTHER INFORMATION: PelB signal sequence

<400> SEQUENCE: 4

Met Lys Tyr Leu Leu Pro Thr Ala Ala Ala Gly Leu Leu Leu Ala
1               5                   10                  15

Ala Gln Pro Ala Met Ala
            20

<210> SEQ ID NO 5
<211> LENGTH: 21
<212> TYPE: PRT
<213> ORGANISM: Artificial Sequence
<220> FEATURE:
<223> OTHER INFORMATION: OmpA signal sequence

<400> SEQUENCE: 5

Met Lys Lys Thr Ala Ile Ala Ile Ala Val Ala Leu Ala Gly Phe Ala
1               5                   10                  15

Thr Val Ala Gln Ala
            20

<210> SEQ ID NO 6
<211> LENGTH: 23
<212> TYPE: PRT
<213> ORGANISM: Artificial Sequence
<220> FEATURE:
<223> OTHER INFORMATION: StII signal sequence

<400> SEQUENCE: 6

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 7
<211> LENGTH: 28
<212> TYPE: PRT
<213> ORGANISM: Artificial Sequence
<220> FEATURE:
<223> OTHER INFORMATION: Endoxylanase signal sequence

<400> SEQUENCE: 7

Met Phe Lys Phe Lys Lys Lys Phe Leu Val Gly Leu Thr Ala Ala Phe
1               5                   10                  15

Met Ser Ile Ser Met Phe Ser Ala Thr Ala Ser Ala
            20                  25

<210> SEQ ID NO 8
<211> LENGTH: 21
<212> TYPE: PRT
<213> ORGANISM: Artificial Sequence
<220> FEATURE:
<223> OTHER INFORMATION: PhoA signal sequence

<400> SEQUENCE: 8

Met Lys Gln Ser Thr Ile Ala Leu Ala Leu Leu Pro Leu Leu Phe Thr
1               5                   10                  15

Pro Val Thr Lys Ala
            20

<210> SEQ ID NO 9

<211> LENGTH: 22
<212> TYPE: PRT
<213> ORGANISM: Artificial Sequence
<220> FEATURE:
<223> OTHER INFORMATION: OmpF signal sequence

<400> SEQUENCE: 9

Met Met Lys Arg Asn Ile Leu Ala Val Ile Val Pro Ala Leu Leu Val
1               5                   10                  15

Ala Gly Thr Ala Asn Ala
            20

<210> SEQ ID NO 10
<211> LENGTH: 21
<212> TYPE: PRT
<213> ORGANISM: Artificial Sequence
<220> FEATURE:
<223> OTHER INFORMATION: PhoE signal sequence

<400> SEQUENCE: 10

Met Lys Lys Ser Thr Leu Ala Leu Val Val Met Gly Ile Val Ala Ser
1               5                   10                  15

Ala Ser Val Gln Ala
            20

<210> SEQ ID NO 11
<211> LENGTH: 26
<212> TYPE: PRT
<213> ORGANISM: Artificial Sequence
<220> FEATURE:
<223> OTHER INFORMATION: MalE signal sequence

<400> SEQUENCE: 11

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 12
<211> LENGTH: 21
<212> TYPE: PRT
<213> ORGANISM: Artificial Sequence
<220> FEATURE:
<223> OTHER INFORMATION: OmpC signal sequence

<400> SEQUENCE: 12

Met Lys Val Lys Val Leu Ser Leu Leu Val Pro Ala Leu Leu Val Ala
1               5                   10                  15

Gly Ala Ala Asn Ala
            20

<210> SEQ ID NO 13
<211> LENGTH: 20
<212> TYPE: PRT
<213> ORGANISM: Artificial Sequence
<220> FEATURE:
<223> OTHER INFORMATION: Lpp signal sequence

<400> SEQUENCE: 13

Met Lys Ala Thr Lys Leu Val Leu Gly Ala Val Ile Leu Gly Ser Thr
1               5                   10                  15

Leu Leu Ala Gly
            20

-continued

```
<210> SEQ ID NO 14
<211> LENGTH: 25
<212> TYPE: PRT
<213> ORGANISM: Artificial Sequence
<220> FEATURE:
<223> OTHER INFORMATION: LamB signal sequence

<400> SEQUENCE: 14

Met Met Ile Thr Leu Arg Lys Leu Pro Leu Ala Val Ala Val Ala Ala
1               5                   10                  15

Gly Val Met Ser Ala Gln Ala Met Ala
            20                  25

<210> SEQ ID NO 15
<211> LENGTH: 20
<212> TYPE: PRT
<213> ORGANISM: Artificial Sequence
<220> FEATURE:
<223> OTHER INFORMATION: OmpT signal sequence

<400> SEQUENCE: 15

Met Arg Ala Lys Leu Leu Gly Ile Val Leu Thr Thr Pro Ile Ala Ile
1               5                   10                  15

Ser Ser Phe Ala
            20

<210> SEQ ID NO 16
<211> LENGTH: 21
<212> TYPE: PRT
<213> ORGANISM: Artificial Sequence
<220> FEATURE:
<223> OTHER INFORMATION: LTB signal sequence

<400> SEQUENCE: 16

Met Asn Lys Val Lys Cys Tyr Val Leu Phe Thr Ala Leu Leu Ser Ser
1               5                   10                  15

Leu Tyr Ala His Gly
            20

<210> SEQ ID NO 17
<211> LENGTH: 23
<212> TYPE: PRT
<213> ORGANISM: Artificial Sequence
<220> FEATURE:
<223> OTHER INFORMATION: MglB signal sequence

<400> SEQUENCE: 17

Met Asn Lys Lys Val Leu Thr Leu Ser Ala Val Met Ala Ser Met Leu
1               5                   10                  15

Phe Gly Ala Ala Ala His Ala
            20

<210> SEQ ID NO 18
<211> LENGTH: 26
<212> TYPE: PRT
<213> ORGANISM: Artificial Sequence
<220> FEATURE:
<223> OTHER INFORMATION: OppA signal sequence

<400> SEQUENCE: 18

Met Thr Asn Ile Thr Lys Arg Ser Leu Val Ala Ala Gly Val Leu Ala
1               5                   10                  15

Ala Leu Met Ala Gly Asn Val Ala Leu Ala
            20                  25
```

```
<210> SEQ ID NO 19
<211> LENGTH: 25
<212> TYPE: PRT
<213> ORGANISM: Artificial Sequence
<220> FEATURE:
<223> OTHER INFORMATION: RbsB signal sequence

<400> SEQUENCE: 19

Met Asn Met Lys Lys Leu Ala Thr Leu Val Ser Ala Val Ala Leu Ser
1               5                   10                  15

Ala Thr Val Ser Ala Asn Ala Met Ala
            20                  25

<210> SEQ ID NO 20
<211> LENGTH: 22
<212> TYPE: PRT
<213> ORGANISM: Artificial Sequence
<220> FEATURE:
<223> OTHER INFORMATION: Agp signal sequence

<400> SEQUENCE: 20

Met Asn Lys Thr Leu Ile Ala Ala Ala Val Ala Gly Ile Val Leu Leu
1               5                   10                  15

Ala Ser Asn Ala Gln Ala
            20

<210> SEQ ID NO 21
<211> LENGTH: 25
<212> TYPE: PRT
<213> ORGANISM: Artificial Sequence
<220> FEATURE:
<223> OTHER INFORMATION: FkpA signal sequence

<400> SEQUENCE: 21

Met Lys Ser Leu Phe Lys Val Thr Leu Leu Ala Thr Thr Met Ala Val
1               5                   10                  15

Ala Leu His Ala Pro Ile Thr Phe Ala
            20                  25

<210> SEQ ID NO 22
<211> LENGTH: 21
<212> TYPE: PRT
<213> ORGANISM: Artificial Sequence
<220> FEATURE:
<223> OTHER INFORMATION: YtfQ signal sequence

<400> SEQUENCE: 22

Met Trp Lys Arg Leu Leu Ile Val Ser Ala Val Ser Ala Ala Met Ser
1               5                   10                  15

Ser Met Ala Leu Ala
            20

<210> SEQ ID NO 23
<211> LENGTH: 21
<212> TYPE: PRT
<213> ORGANISM: Artificial Sequence
<220> FEATURE:
<223> OTHER INFORMATION: HdeA signal sequence

<400> SEQUENCE: 23

Met Lys Lys Val Leu Gly Val Ile Leu Gly Gly Leu Leu Leu Leu Pro
1               5                   10                  15

Val Val Ser Asn Ala
            20
```

```
<210> SEQ ID NO 24
<211> LENGTH: 29
<212> TYPE: PRT
<213> ORGANISM: Artificial Sequence
<220> FEATURE:
<223> OTHER INFORMATION: HdeB signal sequence

<400> SEQUENCE: 24

Met Asn Ile Ser Ser Leu Arg Lys Ala Phe Ile Phe Met Gly Ala Val
1               5                   10                  15

Ala Ala Leu Ser Leu Val Asn Ala Gln Ser Ala Leu Ala
            20                  25

<210> SEQ ID NO 25
<211> LENGTH: 22
<212> TYPE: PRT
<213> ORGANISM: Artificial Sequence
<220> FEATURE:
<223> OTHER INFORMATION: GlnH signal sequence

<400> SEQUENCE: 25

Met Lys Ser Val Leu Lys Val Ser Leu Ala Ala Leu Thr Leu Ala Phe
1               5                   10                  15

Ala Val Ser Ser His Ala
            20

<210> SEQ ID NO 26
<211> LENGTH: 1743
<212> TYPE: DNA
<213> ORGANISM: Artificial Sequence
<220> FEATURE:
<223> OTHER INFORMATION: pelB-CRM197 fusion with 3' and 5' flanking
      sequence

<400> SEQUENCE: 26
cctctagaaa taattttgtt taactttgga aggagatata catatgaaat acttgctgcc      60
aaccgccgcc gccggcctgc tgctgctcgc agcacagccg gctatggcag gtgcggatga    120
tgttgtggac agctctaagt cttttgtgat ggaaaacttt agctcgtacc acggtacgaa    180
gccaggttat gtcgacagca ttcaaaaagg tatccagaaa ccgaagtccg gcacgcaggg    240
taactacgac gacgattgga aagagttcta cagcaccgac aacaagtatg acgcagcggg    300
ttacagcgtt gacaatgaga atccgttgag cggcaaagcg ggtggtgttg tcaaagtgac    360
gtatccgggt ctgaccaagg tcctggcgtt gaaagttgat aacgcggaaa ccattaagaa    420
agagctgggt ctgagcctga ccgagccgtt gatggagcaa gttggtaccg aagagtttat    480
caaacgtttc ggcgatggtg cgagccgcgt tgtcctgtcc ctgccttttg cggagggcag    540
ctccagcgtt gagtatatca ataactggga gcaagcaaaa gcgctgtccg tcgaactgga    600
aatcaatttt gaaacgcgcg gtaaacgtgg tcaagatgca atgtacgagt atatggccca    660
ggcctgcgct ggtaatcgtg ttcgtcgcag cgttggtagc agcttgtctt gtatcaacct    720
ggattgggat gtgatccgtg ataagaccaa gactaagatc gagagcctga agaacatgg     780 cccgattaag aacaagatgt cggagagccc gaataagacc gtgagcgaag aaaaggccaa    840
gcagtatctg gaagagttcc accaaacggc tctggagcat ccggagctga gcgagctgaa    900
aacggttacg ggcaccaacc cggtgttcgc aggtgcgaat tacgcggcgt gggcagtgaa    960
tgtggcgcag gtcatcgact ccgaaacggc ggacaatttg gagaaaacca ccgcagcgct   1020
gagcattctg ccgggcatcg gcagcgttat gggcattgca gatggtgctg tgcaccataa   1080
```

```
cactgaagaa atcgtagcgc aaagcattgc cctgtctagc ttgatggtgg cgcaggctat   1140
tccgctggtc ggcgaactgg ttgatatcgg ctttgctgcc tacaacttcg ttgaaagcat   1200
cattaacctg tttcaggtgg tccacaacag ctataatcgc ccagcgtaca gcccgggtca   1260
caagacccaa ccgttcctgc acgatggcta tgcggtgtct tggaacacgg tcgaagatag   1320
catcattcgt accggtttcc agggcgagag cggccatgac atcaagatta ctgcagaaaa   1380 tacccccgctg ccgatcgcag gtgtcctgct gcctacgatt ccgggtaagc tggacgttaa   1440
caaaagcaaa acccacattt ctgtgaacgg tcgtaagatt cgcatgcgtt gtcgtgcgat   1500
tgacggcgac gtcaccttct gccgtccgaa gagcccggtc tacgttggta atggtgtgca   1560
cgcgaacctg cacgtggcgt ttcaccgcag cagctcggag aaaatccata gcaatgagat   1620
ttctagcgac agcattggcg ttctgggtta ccaaaagacg gttgaccata ccaaagtcaa   1680
ttccaaactg agcctgttct ttgagatcaa aagctaactc gagccccaag ggcgacaccc   1740
cct                                                                 1743
```

<210> SEQ ID NO 27
<211> LENGTH: 33
<212> TYPE: DNA
<213> ORGANISM: Artificial Sequence
<220> FEATURE:
<223> OTHER INFORMATION: PCR sense primer (pelB-CRM197)

<400> SEQUENCE: 27
ggagatatac atatgaaata cttgctgcca acc                                 33

<210> SEQ ID NO 28
<211> LENGTH: 39
<212> TYPE: DNA
<213> ORGANISM: Artificial Sequence
<220> FEATURE:
<223> OTHER INFORMATION: PCR antisense primer (PelB-CRM197)

<400> SEQUENCE: 28
ctttgttagc agccgattag cttttgatct caaagaaca                           39

<210> SEQ ID NO 29
<211> LENGTH: 38
<212> TYPE: DNA
<213> ORGANISM: Artificial Sequence
<220> FEATURE:
<223> OTHER INFORMATION: PCR sense primer (OmpA-CRM197)

<400> SEQUENCE: 29
gctaccgtag cgcaggccgg tgcggatgat gttgtgga                            38

<210> SEQ ID NO 30
<211> LENGTH: 39
<212> TYPE: DNA
<213> ORGANISM: Artificial Sequence
<220> FEATURE:
<223> OTHER INFORMATION: PCR antisense primer (OmpA-CRM197)

<400> SEQUENCE: 30
ctttgttagc agccgattag cttttgatct caaagaaca                           39

<210> SEQ ID NO 31
<211> LENGTH: 75
<212> TYPE: DNA
<213> ORGANISM: Artificial Sequence
<220> FEATURE:

<223> OTHER INFORMATION: PCR sense primer 2 (OmpA-CRM197)

<400> SEQUENCE: 31
ggagatatac atatgaaaaa gacagctatc gcgattgcag tggcactggc tggtttcgct    60
accgtagcgc aggcc    75

<210> SEQ ID NO 32
<211> LENGTH: 39
<212> TYPE: DNA
<213> ORGANISM: Artificial Sequence
<220> FEATURE:
<223> OTHER INFORMATION: PCR antisense primer 2 (OmpA-CRM197)

<400> SEQUENCE: 32
ctttgttagc agccgattag cttttgatct caaagaaca    39

<210> SEQ ID NO 33
<211> LENGTH: 31
<212> TYPE: DNA
<213> ORGANISM: Artificial Sequence
<220> FEATURE:
<223> OTHER INFORMATION: PCR sense primer 3 (OmpA-CRM197)

<400> SEQUENCE: 33
ggagatatac atatgaaaaa gacagctatc g    31

<210> SEQ ID NO 34
<211> LENGTH: 39
<212> TYPE: DNA
<213> ORGANISM: Artificial Sequence
<220> FEATURE:
<223> OTHER INFORMATION: PCR antisense primer 3 (OmpA-CRM197)

<400> SEQUENCE: 34
ctttgttagc agccgattag cttttgatct caaagaaca    39

<210> SEQ ID NO 35
<211> LENGTH: 45
<212> TYPE: DNA
<213> ORGANISM: Artificial Sequence
<220> FEATURE:
<223> OTHER INFORMATION: PCR sense primer (OmpF-CRM197)

<400> SEQUENCE: 35
gttagtagca ggtactgcaa acgctggtgc ggatgatgtt gtgga    45

<210> SEQ ID NO 36
<211> LENGTH: 39
<212> TYPE: DNA
<213> ORGANISM: Artificial Sequence
<220> FEATURE:
<223> OTHER INFORMATION: PCR antisense primer (OmpF-CRM197)

<400> SEQUENCE: 36
ctttgttagc agccgattag cttttgatct caaagaaca    39

<210> SEQ ID NO 37
<211> LENGTH: 78
<212> TYPE: DNA
<213> ORGANISM: Artificial Sequence
<220> FEATURE:
<223> OTHER INFORMATION: PCR sense primer 2 (OmpF-CRM197)

<400> SEQUENCE: 37
ggagatatac atatgatgaa gcgcaatatt ctggcagtga tcgtccctgc tctgttagta    60

```
gcaggtactg caaacgct                                              78

<210> SEQ ID NO 38
<211> LENGTH: 39
<212> TYPE: DNA
<213> ORGANISM: Artificial Sequence
<220> FEATURE:
<223> OTHER INFORMATION: PCR antisense primer 2 (OmpF-CRM197)

<400> SEQUENCE: 38
ctttgttagc agccgattag cttttgatct caaagaaca                        39
```